United States Patent
Hagel et al.

(10) Patent No.: US 8,603,737 B2
(45) Date of Patent: Dec. 10, 2013

(54) METHODS FOR IDENTIFYING HCV PROTEASE INHIBITORS

(75) Inventors: Margit Hagel, Roslindale, MA (US); Thia B. St. Martin, Lunenburg, MA (US); Mariana S. Nacht, Belmont, MA (US)

(73) Assignee: Celgene Avilomics Research, Inc., Bedford, MA (US)

( * ) Notice: Subject to any disclaimer, the term of this patent is extended or adjusted under 35 U.S.C. 154(b) by 695 days.

(21) Appl. No.: 12/563,087

(22) Filed: Sep. 18, 2009

(65) Prior Publication Data

US 2010/0074890 A1 Mar. 25, 2010

Related U.S. Application Data

(60) Provisional application No. 61/098,681, filed on Sep. 18, 2008, provisional application No. 61/170,795, filed on Apr. 20, 2009.

(51) Int. Cl.
*C12Q 1/70* (2006.01)

(52) U.S. Cl.
USPC .......................................................... 435/5

(58) Field of Classification Search
None
See application file for complete search history.

(56) References Cited

U.S. PATENT DOCUMENTS

| | | | |
|---|---|---|---|
| 6,828,550 B2 * | 12/2004 | Griffey et al. | 250/281 |
| 6,846,806 B2 * | 1/2005 | Priestley | 530/330 |
| 7,125,845 B2 * | 10/2006 | Wu et al. | 424/85.4 |
| 7,705,138 B2 * | 4/2010 | Lin et al. | 536/23.2 |
| 2009/0176858 A1 | 7/2009 | Niu et al. | |
| 2009/0306085 A1 | 12/2009 | Petter et al. | |
| 2010/0041591 A1 | 2/2010 | Niu et al. | |
| 2010/0041674 A1 | 2/2010 | Niu et al. | |
| 2010/0069294 A1 | 3/2010 | Petter et al. | |

OTHER PUBLICATIONS

Boguszewska-Chachulska et al. Searching for a new anti-HCV therapy: Synthesis and properties of tropolone derivatives. Biochemical and Biophysical Research Communications 341 (2006) 641-647.*
Lohmann et al. Replication of Subgenomic Hepatitis C Virus RNAs in a Hepatoma Cell Line. Science. 285, 100 (1999).*
Boguszewska-Chachulska et al. Direct fluorometric measurement of hepatitis C virus helicase activity. FEBS Letters. 567 (2004): 253-258.*
Alberti, A. et al., *J. Hepatology* 31., (Suppl. 1): 17-24, 1999.
Blight, K.J. et al., *Antiviral Ther.* 3, Suppl. 3: 71-81, 1998.
Gould EA, Solomon T. Pathogenic flaviviruses. *Lancet.*, 371(9611):500-9, 2008.
Hepatitis C Support Project, "HCV: Genotype & Quasispecies", Version 2.0, pp. 1-3, Feb. 2006.
Huang, J.F., et al., *J Viral Hepatitis* 13(6), 396-401, 2006.
Hung, C.H., et al., *J Viral Hepatitis* 13(6), 409-414, 2006.
Lin et al., *In Vitro Resistance Studies of HCV Serine Protease Inhibitors*, JBC, vol. 279, No. 17, 17508-17514, 2004.
Kou et al. *JVirol*, 81, 7999, 2007.
Krieger et al. *JVirol*, 75, 4614, 2001.
Lescar, J et al., *Antiviral Res.*, vol. 80, 94-101, 2008.
Lohmann, V et al., *J. Virol.*, vol. 77, No. 5, 3007-3019, 2003.
Miller et al., *PNAS*, vol. 87, 2057-2061,1990.
Moradpour, D., et al., Eur. J. Gastroenterol. Hepatol. 11: 1199-1202, 1999.
Shoji et al., *Virology*, 254, 315-323, 1999.
Simmonds et al., *Hepatology*, vol. 42, No. 4, 2005.
Mukhopadhyay, Suchetana, et al., "A structural perspective of the flavivirus life cycle," *Nature Reviews Microbiology* 3, 13-22, 2005.
Tautz et al., *J. Virol.*, vol. 71, 7, 5415-5422, 1997.
Walker, M.A., et al., *DDT 4*: 518-29, 1999.
Weiland, O., *FEMS Microbiol. Rev.* 14, 279-88, 1994.
Yang et al., *Virology*, 268, 132-140, 2000.

\* cited by examiner

*Primary Examiner* — Michelle S Horning
(74) *Attorney, Agent, or Firm* — Choate, Hall & Stewart LLP; Andrea L. C. Robidoux; John P. Rearick

(57) ABSTRACT

The present invention provides methods for identifying compounds useful as HCV protease inhibitors.

23 Claims, 7 Drawing Sheets

US 8,603,737 B2

METHODS FOR IDENTIFYING HCV PROTEASE INHIBITORS

CROSS REFERENCE TO RELATED APPLICATIONS

The present invention claims priority to U.S. provisional application Ser. No. 61/098,681, filed Sep. 19, 2008, and U.S. provisional application Ser. No. 61/170,795, filed Apr. 20, 2009, the entirety of each of which is hereby incorporated by reference.

TECHNICAL FIELD OF THE INVENTION

The present invention relates to methods of identifying compounds useful as inhibitors of HCV protease.

BACKGROUND OF THE INVENTION

It is estimated that over 170 million people worldwide are infected with the Hepatitis C virus (HCV). With an estimated human sero-prevalence of 3% globally, HCV is the major cause for most cases of non-A, non-B hepatitis, (Alberti, A. et al., *J. Hepatology* 31., (Suppl. 1): 17-24, 1999). While the symptoms of acute hepatitis subside in some patients, at least 85% of HCV infections become chronic, and 20% of those infected develop liver cirrhosis. There is less than a 50% survival rate at four years post cirrhosis diagnosis. Chronic HCV infection is also associated with increased incidence of hepatocellular carcinoma.

HCV is a positive-stranded RNA virus whose genome encodes a polyprotein of approximately 3000 amino acids. This precursor protein is processed into at least 10 viral structural and nonstructural proteins: C, E1, E2, p7, NS2, NS3, NS4A, NS4B, NS5A, and NS5B (Blight, K. J., et al., Antiviral Ther. 3, Suppl. 3: 71-81, 1998). HCV nonstructural (NS) proteins are derived by proteolytic processing of the polyprotein and are presumed to provide the essential catalytic machinery for viral replication.

NS3 is an approximately 68 Kda protein, and has both an N-terminal serine protease domain and an NTPase/helicase domain at its C-terminus. It has been shown that the NS4A protein serves as a co-factor for the serine protease activity of NS3. NS3 functions as a proteolytic enzyme that is involved in processing the viral polyprotein to liberate other nonstructural proteins necessary for HCV replication, and is a viable therapeutic target for antiviral chemotherapy. Internal self-cleavage of NS3 in its helicase domain also occurs, and this activity is dependent on both NS4a and NS3 protease activity.

Current methods for assaying inhibition of HCV protease rely on the indirect measurement HCV NS3 protease activity by measuring viral RNA replication in a Huh-7 replicon assay, often by utilizing secondary "reporters." For example, luciferase is often utilized as a reporter to indicate the number of viral RNA molecules in a cell. Inhibition of NS3 protease activity leads to inhibition of viral replication, over time, and can be measured by decreased luciferase expression. However, to date, the direct measurement of HCV protease into its self-cleavage products has not been reported.

No vaccines are available for HCV, and the established therapy of interferon treatment is effective in only 15-20% of patients (Weiland, O., FEMS Microbiol. Rev. 14: 279-88, 1994), and has significant side effects (Walker, M. A., et al., DDT 4: 518-29, 1999; Moradpour, D., et al., Eur. J. Gastroenterol. Hepatol. 11: 1199-1202, 1999). While the current standard of care, pegylated interferon α in combination with ribavirin, is more efficacious and appears to decrease hepatocellular carcinoma in patients with HCV-related cirrhosis (Hung, C. H., et al., J Viral Hepatitis 13(6): 409-414, 2006), this treatment has also been shown to produce side effects such as thyroid dysfunction (Huang, J. F., et al., J Viral Hepatitis 13(6): 396-401, 2006).

The poor prognosis for patients suffering from HCV infection and the current lack of effective, approved treatments, highlights the overwhelming need for new inhibitors of HCV NS3 protease and methods for identifying the same.

SUMMARY OF THE INVENTION

In certain embodiments, the present invention provides a method for identifying inhibitors of HCV protease. In some embodiments, such methods comprise directly measuring internal self-cleavage of HCV NS3 protease in the presence of a test compound as compared to internal self-cleavage of HCV NS3 protease in the absence of said test compound.

In other aspects, the present invention provides compounds identified as inhibitors of HCV NS3 protease by methods of the present invention. Such HCV NS3 protease inhibitors identified by methods of the present invention, and pharmaceutically acceptable compositions thereof, are useful for treating a variety of diseases, disorders or conditions, associated with HCV. Such diseases, disorders, or conditions include those described herein.

BRIEF DESCRIPTION OF THE DRAWINGS

FIG. 6 depicts that, even with this mutation, irreversible covalent drugs can inhibit activity from the mutant protease for at least 24 hours after compound removal.

DETAILED DESCRIPTION OF CERTAIN EMBODIMENTS

Figure 1:
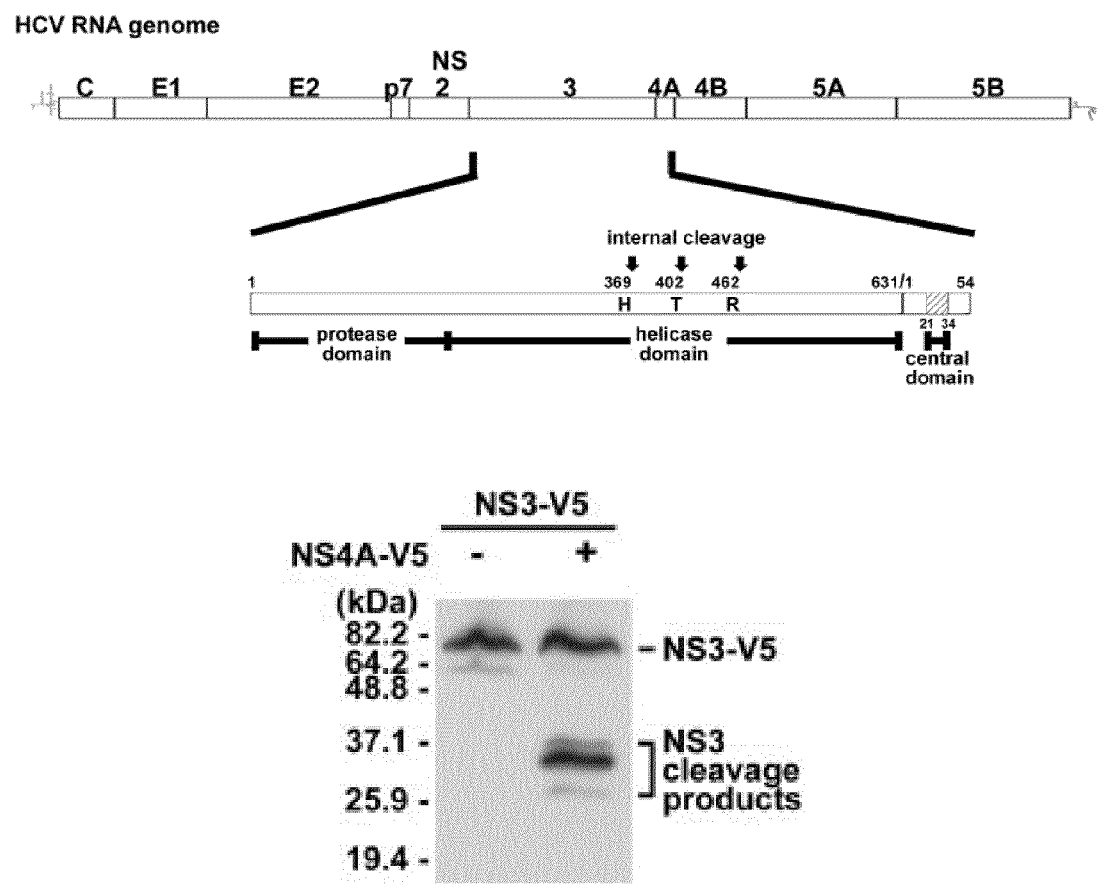
FIG. 1 depicts, at the top, the HCV RNA genome with the NS3 internal cleavage sites at amino acids 369, 402 and 462 identified. The bottom Western blot depicts the NS3 self-cleavage products in the presence of NS4A.

HCV NS3 is a protease that cleaves the viral polyprotein into individual non-structural proteins downstream of NS3 (Kou et al. J Virol (2007). 81:7999). In genotype 1b, described in detail below, NS3 also cleaves itself within the helicase domain of the holoenzyme. This activity is dependent on the NS3 protease activity itself and the presence of the viral NS3 cofactor known as NS4A. This cleavage, and its resulting products, is depicted in FIG. 1. As is apparent from FIG. 1, the cleavage of HCV NS3 protease is amenable to visualization by immunoblotting or ELISA. Current methods for assaying inhibition of HCV protease rely on the indirect measurement HCV NS3 self-cleavage, for example by the use of secondary "reporters." One such method is the replicon method. The replicon system is a human hepatoma cell line transfected with subgenomic selectable HCV-RNA. The HCV-RNA replicates autonomously in this system, but requires the activity of the viral NS3 protease. Self replication can be measured by quantitating replicon RNA, or by using a replicon system with a built-in reporter gene such as luciferase (Krieger et al. J Virol (2001) 75:4614). Replicon cell lines are usually exposed to protease inhibitors continuously for 72 hours, at which time reporter activity (or RNA quantity) is evaluated.

Figure 2A:
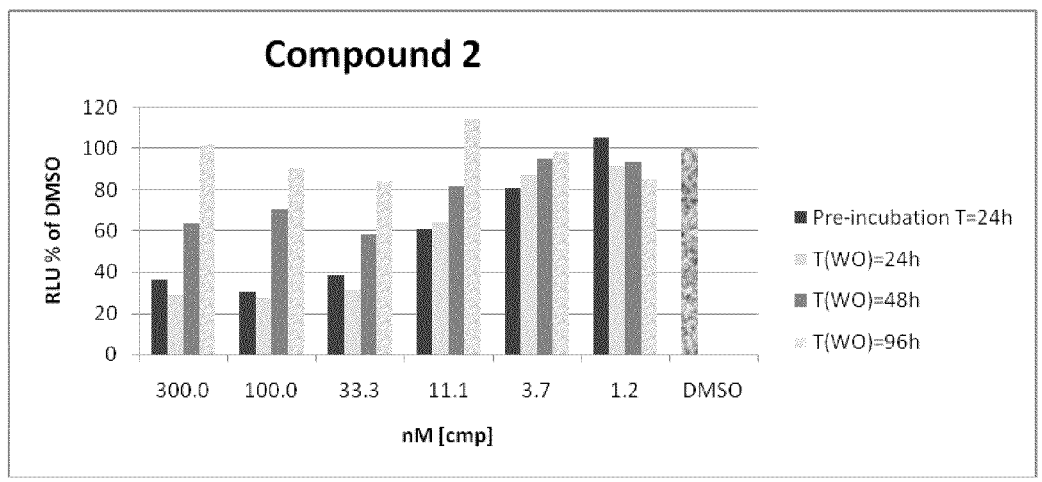
FIG. 2 depicts luciferase activity, using a replicon assay, in the presence of varying concentrations of two HCV protease inhibitors, Compound 2 and Compound 3, at 24 h, 48 h and 96 h. Compound 2 is a non-covalent inhibitor whereas Compound 3 is an irreversible covalent inhibitor. Despite differences in the mechanism of action of the two compounds on the protease, the replicon assay shows similar results, due to the indirect nature of the assay readout.
Figure 2B:
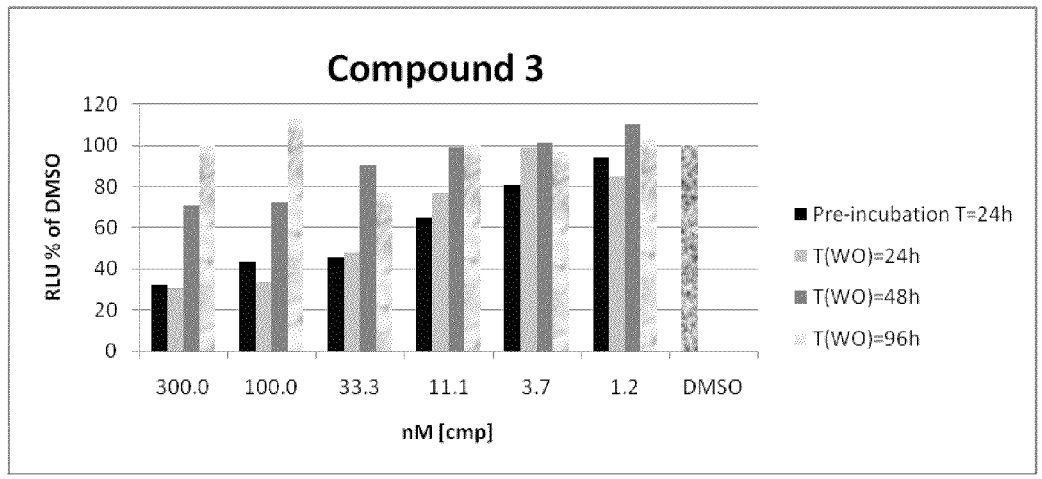

This replicon assay method proved inadequate to study prolonged duration of action by covalent irreversible protease inhibitors. The replicon system is dependent on NS3 protease activity to allow for continued HCV-RNA replication, and the protease protein has a half-life of approximately 16 hours. Moreover, the replicon cells have abundant HCV-RNA at the time that the protease inhibitor is introduced. The HCV-RNA also has a long half-life, and while there is HCV-RNA present, HCV proteins, including the NS3 protease, will be continuously translated. Thus, it is not possible to see prolonged duration of action against the HCV NS3 protease unless the RNA/luciferase and protease half-lives are uncoupled. Indeed, this phenomenon was observed when this replicon method was utilized to assay irreversible inhibitors of HCV NS3 protease. It was observed that previously confirmed covalent irreversible inhibitors showed no prolonged duration of action as measured by luciferase. (See FIG. 2a and FIG. 2b).

To address the need for an assay suitable for detecting prolonged duration of action, the present invention provides an assay method which directly measures the internal self-cleavage activity of NS3-containing protein. In certain embodiments, the present invention provides a method comprising the steps of:

(a) contacting a test compound with an NS3-containing protein; and
(b) directly measuring a level of internal self-cleavage of the NS3.

In some embodiments, the NS3-containing protein is HCV NS3. Thus, in certain embodiments, the present invention provides a method comprising the steps of:

(a) contacting a test compound with an HCV NS3; and
(b) measuring internal self-cleavage of the HCV NS3 as compared to self-cleavage of the HCV NS3 in the absence of said test compound.

It will be appreciated that inhibition of NS3 would lead to an increase in NS3 and a decrease in cleavage products. Thus, one of ordinary skill in the art will recognize that, in certain embodiments, the measurement of self-cleavage of the HCV NS3 is performed by measuring at least one of: a change in the amount of HCV NS3; and/or a change in the amount of HCV NS3 self cleavage products.

In some embodiments, the measurement of self-cleavage of the HCV NS3 is performed by measuring at least one of:
(a) an increase in HCV NS3; and
(b) a decrease of HCV NS3 self-cleavage products.

In other embodiments, the measurement of self-cleavage of the HCV NS3 is performed by measuring at least one of:
(a) a decrease in HCV NS3; and
(b) an increase of HCV NS3 self-cleavage products.

As described generally above, the present invention provides methods for identifying compounds that inhibit HCV NS3. It will be appreciated that the methods may be used to identify inhibitors of any HCV NS3 polyprotein. In some embodiments, the polyprotein is NS3. In other embodiments, the polyprotein is NS3-NS4A.

In certain embodiments, methods of the present invention are used to identify reversible inhibitors of HCV NS3. In other embodiments, methods of the present invention are used to identify covalent irreversible inhibitors of HCV NS3. In some embodiments, methods of the present invention are used to determine duration of inhibition. Duration of inhibition is an important factor in determining appropriate dosing of an inhibitor for treatment of a disorder associated with HCV. For example, prolonged duration of inhibition of HCV NS3, as determined by provided methods, is a factor supportive of once-daily dosing. Exemplary such inhibitors are described herein.

HCV is an extremely variable virus that forms polymorphic swarms of variants within the host. Worldwide, several different genotypes have now been defined (Simmonds et al., Hepatology, Vol. 42, No. 4, 2005). These genotypes have been further classified into more closely related, genetically distinct subtypes. Comparative sequence portions, known as consensus sequences, are set forth in Table 1, below. HCV genotypes and subtypes are distributed differently in different parts of the world, and certain genotypes predominate in certain areas. Genotypes 1-3 are widely distributed throughout the world. Subtype 1a is prevalent in North and South America, Europe, and Australia. Subtype 1b is common in North America and Europe, and is also found in parts of Asia. Genotype 2 is present in most developed countries, but is less common than genotype 1 (www.hcvadvocate.org/hepatitis/factsheets_pdf/genotype_FS.pdf). Other genotypes are prevalent in ex-US patient populations and are therefore important targets. Thus, in certain embodiments, a provided method utilizes an HCV NS3 selected from any genotype and subtype listed in Table 1, below.

Notably, a cysteine located at amino acid position 159 in genotype 1b is conserved in all genotypes and subtypes of HCV NS3 sequenced to date, although the amino acid position may be different in other genotypes and subtypes. Targeting this cysteine residue with covalent irreversible inhibitors should enable the development of agents which are effective against multiple HCV genotypes.

As described herein, the present invention provides a method for identifying covalent irreversible inhibitors of one or more HCV protease genotypes, and variants thereof. In some embodiments, an irreversible inhibitor of one or more HCV protease genotypes, and variants thereof, comprises a warhead group capable of covalently binding to a cysteine residue thereby irreversibly inhibiting the enzyme. Such warhead groups are described in detail in U.S. patent application U.S. Ser. No. 12/339,680, filed Dec. 19, 2008, United States patent application publication 2009/0176858, and International patent application publications WO 2009/082697 and WO 2009/082701, the entirety of which is hereby incorporated herein by reference. In some embodiments, one or more genotypes inhibited by compounds identified by methods of the present invention include 1a, 1b, 2a, and 3a. In certain embodiments, one or more such variants include genotype 1b mutations in the NS3 protease of A156T, A156S, D168V, D168A, and R155K.

Thus, in certain embodiments, the HCV NS3 for use in methods of the present invention is selected from any of the genotypes and subtypes listed in Table 1, below. In some embodiments, the HCV NS3 for use in methods of the present invention is selected from genotypes 1a, 1b, 2a, and 3a. In other embodiments, the HCV NS3 for use in methods of the present invention is a variant selected from genotype 1b mutations in the NS3 protease of A156T, A156S, D168V, D168A, and R155K.

One of ordinary skill in the art will appreciate that HCV protease genotypes and variants thereof have one or more cysteine residues near the binding domain. Without wishing to be bound by any particular theory, it is believed that proximity of a warhead group to the cysteine of interest facilitates covalent modification of that cysteine by the warhead group. In some embodiments, the cysteine residue of interest is Cys159 of HCV protease subtype 1b, or a variant thereof, where the provided residue numbering is in accordance with Uniprot (code Q91RS4). Cysteine residues of other HCV protease genotypes and subtypes suitable for covalent modification by irreversible inhibitors identified by methods of the present invention include those summarized in Table 1, below, where the bold and underlined "C" refers to a cysteine residue conserved at an equivalent position to Cys159 of HCV protease subtype 1b.

TABLE 1[y]

| HCV genotype/ subtype | Representative Sequence Portion[a] | Patient ID | Sequence Identifier |
|---|---|---|---|
| 1a | GHAVGLFRAAVCTRGVAKAV | _.H77.NC_004102 | SEQ ID NO: 1 |
| 1a | GHAVGIFRAAVCTRGVAKAV | CH.BJD-V271.EU482858 | SEQ ID NO: 2 |
| 1a | GHAVGIFRAAVCTRGVAKAV | DE.BJD-V25.EU482831 | SEQ ID NO: 3 |
| 1a | GHAVGLFRAAVCTRGVAKAV | US.H77-H21.AF011753 | SEQ ID NO: 4 |
| 1b | GHAVGIFRAAVCTRGVAKAV | AU.HCV-A.AJ000009 | SEQ ID NO: 5 |
| 1b | GHVVGIFRAAVCTRGVAKAV | CH.BJD-V272.EU482859 | SEQ ID NO: 6 |
| 1b | GHAVGIFRAAVCTRGVAKAV | JP.HCV-BK.M58335 | SEQ ID NO: 7 |
| 1c | GHAVGIFRAAVCTRGVAKAV | JD.HC-G9.D14853 | SEQ ID NO: 8 |
| 1c | GHVAGIFRAAVCTRGVAKAV | IN.AY051292.AY051292 | SEQ ID NO: 9 |
| 2a | GHAVGIFRAAVCSRGVAKSI | JP.AY746460.AY746460 | SEQ ID NO: 10 |
| 2a | GHAVGIFRAAVCSRGVAKSI | JP.JCH-6.AB047645 | SEQ ID NO: 11 |
| 2a | GHAVGIFRAAVCSRGVAKSI | _.G2AK1.AF169003 | SEQ ID NO: 12 |
| 2b | GHAVGLFRAAVCARGVAKSI | JP.HC-J8.D10988 | SEQ ID NO: 13 |
| 2b | GHAVGLFRAAVCARGVAKSI | JP.MD2b1-2.AY232731 | SEQ ID NO: 14 |
| 2c | GHAVGIFRAAVCSRGVAKSI | _.BEBE1.D50409 | SEQ ID NO: 15 |
| 2i | AHAVGIFRAAVCSRGVAKSI | VN.D54.DQ155561 | SEQ ID NO: 16 |
| 2k | GHAVGIFRAAICTRGAAKSI | MD.VAT96.AB031663 | SEQ ID NO: 17 |
| 3a | GHVAGIFRAAVCTRGVAKAL | CH.452.DQ437509 | SEQ ID NO: 18 |
| 3a | GHVAGIFRAAVCTRGVAKAL | DE.HCVCENS1.X76918 | SEQ ID NO: 19 |
| 3a | GHVAGIFRAAVCTRGVAKAL | ID.ps23.EU315121 | SEQ ID NO: 20 |
| 3b | GHVMGIFIAVVCTRGVAKAL | IN.RG416.DQ284965 | SEQ ID NO: 21 |
| 3b | GHVVGIFRAAVCTRGVAKAL | JP.HCV-Tr.D49374 | SEQ ID NO: 22 |
| 3k | GHVAGIFRAAVCTRGVAKAL | ID.JK049.D63821 | SEQ ID NO: 23 |
| 4a | GHAAGIFRAAVCTRGVAKAV | EG.Eg9.DQ988077 | SEQ ID NO: 24 |
| 4a | GHAAGLFRAAVCTRGVAKAV | _.01-09.DQ418782 | SEQ ID NO: 25 |

TABLE 1′-continued

| HCV genotype/ subtype | Representative Sequence Portion[a] | Patient ID | Sequence Identifier |
|---|---|---|---|
| 4a | GHAAGLFRAAVCTRGVAKAV | _.F753.DQ418787 | SEQ ID NO: 26 |
| 4d | GHAAGIFRAAVCTRGVAKAV | _.03-18.DQ418786 | SEQ ID NO: 27 |
| 4d | GHAAGIFRAAVCTRGVAKTV | _.24.DQ5 16083 | SEQ ID NO: 28 |
| 4f | GHAVGIFRAAVCTRGVAKAV | FR.IFBT84.EF589160 | SEQ ID NO: 29 |
| 4f | GHAVGIFRAAVCTRGVAKAV | FR.IFBT88.EF589161 | SEQ ID NO: 30 |
| 5a | GHVVGVFRAAVCTRGVAKAL | GB.EUH1480.Y13184 | SEQ ID NO: 31 |
| 5a | GHVVGVFRAAVCTRGVAKAL | ZA.5A13.AF064490 | SEQ ID NO: 32 |
| 6a | GHVVGLFRAAVCTRGVAKSL | HK.6a74.DQ480524 | SEQ ID NO: 33 |
| 6a | GHVVGLFRAAVCTRGVAKSL | HK.6a77.DQ480512 | SEQ ID NO: 34 |
| 6a | GHVVGLFRAAVCTRGVAKSL | HK.EUHK2.Y12083 | SEQ ID NO: 35 |
| 6b | GHVVGLFRAAVCTRGVAKAL | _.Th580.NC_009827 | SEQ ID NO: 36 |
| 6c | GHVVGLFRAAVCTRGVAKAL | TH.Th846.EF424629 | SEQ ID NO: 37 |
| 6d | DHVVGLFRAAVCTRGVAKAL | VN.VN235.D84263 | SEQ ID NO: 38 |
| 6e | GHVVGLFRAAVCTRGVAKAI | CN.GX004.DQ314805 | SEQ ID NO: 39 |
| 6f | GHAVGIFRAAVCTRGVAKAI | TH.C-0044.DQ835760 | SEQ ID NO: 40 |
| 6f | GHAVGIFRAAVCTRGVAKAI | TH.C-0046.DQ835764 | SEQ ID NO: 41 |
| 6g | GHVVGLFRAAVCTRGVAKAL | HK.HK6554.DQ314806 | SEQ ID NO: 42 |
| 6g | GHVVGLFRAAVCTRGVAKAL | ID.JK046.D63822 | SEQ ID NO: 43 |
| 6h | GHVAGIFRAAVCTRGVAKSL | VN.VN004.D84265 | SEQ ID NO: 44 |
| 6i | GHVAGIFRAAVCTRGVAKSL | TH.C-0159.DQ835762 | SEQ ID NO: 45 |
| 6j | GHVAGIFRAAVCTRGVAKSL | TH.C-0667.DQ835761 | SEQ ID NO: 46 |
| 6j | GHVAGIFRAAVCTRGVAKSL | TH.Th553.DQ835769 | SEQ ID NO: 47 |
| 6k | GHVAGIFRAAVCTRGVAKSL | CN.KM41.DQ278893 | SEQ ID NO: 48 |
| 6k | GHVAGIFRAAVCTRGVAKSL | CN.KM45.DQ278891 | SEQ ID NO: 49 |
| 6k | GHVAGIFRAAVCTRGVAKSL | VN.VN405.D84264 | SEQ ID NO: 50 |
| 6l | GHVAGIFRAAVCTRGVAKSL | US.537796.EF424628 | SEQ ID NO: 51 |
| 6m | GHAVGVFRAAVCTRGVAKSL | TH.C-0185.DQ835765 | SEQ ID NO: 52 |
| 6m | GHAVGVFRAAVCTRGVAKSL | TH.C-0208.DQ835763 | SEQ ID NO: 53 |
| 6n | GHVVGIFRAAVCTRGVAKSL | CN.KM42.DQ278894 | SEQ ID NO: 54 |
| 6n | GHVVGIFRAAVCTRGVAKSL | TH.D86/93.DQ835768 | SEQ ID NO: 55 |
| 6o | GHAVGLFRAAVCTRGVAKAI | CA.QC227.EF424627 | SEQ ID NO: 56 |
| 6p | GHVVGLFRAAVCTRGVAKAI | CA.QC216.EF424626 | SEQ ID NO: 57 |
| 6q | GHAVGLFRAAVCTRGVAKAI | CA.QC99.EF424625 | SEQ ID NO: 58 |
| 6t | GHVVGLFRAAVCTRGVAKAI | VN.TV241.EF632069 | SEQ ID NO: 59 |
| 6t | GHVVGLFRAAVCTRGVAKAI | VN.TV249.EF632070 | SEQ ID NO: 60 |

TABLE 1<sup>y</sup>-continued

| HCV genotype/ subtype | Representative Sequence Portion<sup>a</sup> | Patient ID | Sequence Identifier |
|---|---|---|---|
| 6t | GHVVGLFRAAV<u>C</u>TRGVAKAI | VN.VT21.EF632071 | SEQ ID NO: 61 |
| 7a | SHCVGIFRAAV<u>C</u>TRGVAKAV | CA.QC69.EF108306 | SEQ ID NO: 62 |

<sup>y</sup>It will be appreciated by one of ordinary skill in the art that every virus is prone to mutation and subject to polymorphisms, and any genotype consensus sequences described herein are representative of a given genotype or subtype. Such representative consensus sequences are available at hcv.lanl.gov/content/sequence/NEWALIGN/align.html.

In certain embodiments, provided methods for identifying compounds that inhibit HCV NS3 protease are used in combination with other methods used to assay inhibitory activity of test compounds. For example, a provided method may be utilized in combination with additional methods useful for determining whether a compound is an irreversible inhibitor with prolonged duration of action. Such methods include washout experiments and mass spectrometric analysis of the protein-inhibitor conjugate. Thus, in certain embodiments, the present invention provides a method comprising the steps of:
(a) contacting a cell with a test compound;
(b) washing said cells at one or more time intervals; and
(c) measuring internal self-cleavage of the HCV NS3 as compared to self-cleavage of HCV NS3 in the absence of said test compound.

In some embodiments, the measuring step is performed by measuring at least one of: (a) a decrease in HCV NS3; and (b) an increase of HCV NS3 self-cleavage products. In other embodiments, the measuring step is performed by measuring at least one of: (a) an increase in HCV NS3; and (b) a decrease in HCV NS3 self-cleavage products.

In certain embodiments, the cells are washed at any time point between about 1 and 48 hours. In certain embodiments, the washing step is performed at any one or more of 1 to 48 hours. In some embodiments, the washing step is performed at any one or more of 2, 4, 6, 8, 10, 12, 14, 16, 18, 20, 22, and 24 hours.

One of ordinary skill in the art, having read ensuing Examples 8 and 10, will realize that methods of the present invention can utilize any cell line expressing both NS3 and NS4A. In certain embodiments, the cells are Huh-7-Luc-Neo-ET cells, Huh-9-13 cells, Huh-5-15 cells, Huh-11-7 cells. In some embodiments, the cells are variations of Huh-7-Luc-Neo-ET cells that include NS3 mutations A156T, A156S, D168V, D168A, and R155K.

In addition, it will be appreciated that methods of the present invention can be carried out with a recombinant vector transfected into any cell line that allows expression of NS3 and NS4A. In certain embodiments, the recombinant vector expresses a protein comprising NS3 and NS4A. In certain embodiments, the recombinant vector expresses NS3, NS4a and other polyprotein sequences of HCV such as, but not limited to, NS5.

In some embodiments, the assay may be repeated with a plurality of different concentrations of a test compound. Thus, in certain embodiments, the inhibitory activity of a test compound can be determined by fitting a concentration-dependent inhibition curve. It will also be appreciated that the assay may be repeated with a plurality of different test compounds.

The present invention further provides methods for screening test compounds to identify those that inhibit HCV NS3. In certain embodiments, the methods are carried out in multi-well plates, including, but not limited to, 24-well, 48-well, 96-well, 384-well, and 1536-well plate formats. In certain embodiments, provided methods are used to identify compounds that inhibit HCV protease NS3. In some embodiments, provided methods are used to identify irreversible inhibitors of HCV protease NS3.

Other Suitable Proteases

Viruses which are known to cause Dengue, Japanese encephalitis, West Nile and yellow fever belong to the Flavivirus genus, which is a member of the Flaviviridae family. They are human pathogens that cause large epidemics and tens of thousands of deaths annually in many parts of the world. For example, haemorrhagic disease, encephalitis, biphasic fever, flaccid paralysis, and jaundice are typical manifestations of these diseases in human beings after infections by mosquito-borne or tick-borne flaviviruses (Gould E A, Solomon T. Pathogenic flaviviruses. *Lancet*. 2008 Feb. 9; 371(9611):500-9). The structural organization of these viruses and their associated structural proteins has provided insight into the molecular transitions that occur during the viral life cycle, such as assembly, budding, maturation and fusion (Suchetana Mukhopadhyay, Richard J. Kuhn & Michael G. Rossmann. A structural perspective of the flavivirus life cycle. *Nature Reviews Microbiology* 3, 13-22 (January 2005)).

As described generally above, methods of the present invention are useful for identifying inhibitors of NS3 polyprotein cleavage activity. Similar to the NS3 polyprotein of HCV protease, the multifunctional NS3 polyprotein of flavivirus forms a non-covalent complex with a cofacter, here the NS2B cofactor, and contains the serine-protease activity domain at its N-terminus that is responsible for proteolytic processing of the viral polyprotein. The NS3 of flavivirus has an ATPase/helicase and RNA triphosphatase at its C-terminal end that are essential for RNA replication. In addition, flavivirus NS3 also seems to be involved in virus assembly. See Lescar J, Luo D, Xu T, Sampath A, Lim S P, Canard B, Vasudevan S G. Towards the design of antiviral inhibitors against flaviviruses: The case for the multifunctional NS3 protein from Dengue virus as a target. *Antiviral Res*. 2008 Jul. 30.

Thus, in certain embodiments, the present invention provides a method for identifying inhibitors of flavivirus NS3, comprising the steps of:
(a) providing a test compound;
(b) contacting said test compound with a flavivirus NS3; and
(c) measuring internal self-cleavage of the flavivirus NS3 as compared to self-cleavage of the flavivirus NS3 in the absence of said test compound.

It will be appreciated that inhibition of flavivirus NS3 would lead to an increase in flavivirus NS3 and a decrease in cleavage products. Thus, one of ordinary skill in the art will recognize that, in certain embodiments, the measurement of self-cleavage of the flavivirus NS3 is performed by measuring at least one of: a change in the amount of flavivirus NS3; and/or a change in the amount of flavivirus NS3 self cleavage products.

In some embodiments, the measurement of self-cleavage of the flavivirus NS3 is performed by measuring at least one of:

(a) an increase in flavivirus NS3; and
(b) a decrease of flavivirus NS3 self-cleavage products.

In other embodiments, the measurement of self-cleavage of the flavivirus NS3 is performed by measuring at least one of:

(a) a decrease in flavivirus NS3; and
(b) an increase of flavivirus NS3 self-cleavage products.

In certain embodiments, the flavivirus NS3 is selected from any member of the flavivirus family. In some embodiments, the flavivirus is associated with any of Dengue, Japanese encephalitis, West Nile and yellow fever.

Secondary Ligands

In certain embodiments, a provided method further comprises a step of introducing a secondary ligand that binds specifically to an antibody specific for HCV NS3, or a cleavage product thereof, and wherein the measuring comprises detecting bound secondary ligand. In some embodiments, the secondary ligand is an antibody. In some embodiments, the secondary ligand is biotinylated. In some embodiments, the secondary ligand is conjugated to a "tag" as defined and described herein.

Also, the system itself can be manipulated so that the NS3 product contains tags that are identifiable by an appropriate antibody. Recombinant DNA technology would be utilized to add a tag to one end of the NS3 gene or another in a system that would reengineer the replicon or a portion thereof that contains at least NS3 and NS4A.

In some embodiments, suitable epitope tags include, but are not limited to, V5, Histidine$_6$ FLAG-tag, HA, and c-Myc.

In certain embodiments, for the methods described above, the step of detecting cleavage utilizes a detection technique selected from chemiluminescence, fluorescence, phosphorescence, radioactivity, colorimetry, ultra-violet spectroscopy, and infra-red spectroscopy. In some embodiments, the step of assaying utilizes chemiluminescence. In some embodiments, the step of detecting utilizes a fluorescent marker. In some embodiments, the step of assaying utilizes a radioisotope.

Other techniques, ligands, antibodies, and enzymes are known in the art and may be used in accordance with the present invention, including those described by Hornbeck, P., Curr Protoc Immunol., *Enzyme-Linked Immunosorbent Assays,* 2001 May; Chapter 2, Unit 2.1; Ausubel et al. *Current Protocols in Molecular Biology* (John Wiley & Sons, Inc., New York, 1999); *Molecular Cloning: A Laboratory Manual,* 2nd Ed., ed. by Sambrook, Fritsch, and Maniatis (Cold Spring Harbor Laboratory Press: 1989); *Antibodies: A Laboratory Manual,* E. Harlow and D. Lane, ed., Cold Spring Harbor Laboratory (Cold Spring Harbor, N.Y., 1988), each of which is herein incorporated by reference.

Tags

A "tag" is used herein interchangeably with "label" and is intended to mean at least one element, isotope, or chemical compound that when attached to a moiety or compound enables detection of the moiety or compound to which it is attached. In general, tags typically fall into given classes a) isotopic labels, which may be radiaoctive or heavy isotopes; b) immune labels, which may be antibodies or antigens, which may be bound to enzymes (such as horseradish peroxidase) that produce detectable agents; c) colored, luminescent, phosphorescent, or fluorescent dyes; d) photoaffinity labels; and e) ligands with known binding partners (such as biotin-streptavidin, FK506-FKBP, etc.). It will be appreciated that the tag may be incorporated into the HCV protease at any suitable position.

In some embodiments of the invention, the tag is a radio-label. Radioactive isotopes that may be used as radiolabels include, but are not limited to, $^2$H, $^3$H, $^{13}$C, $^{14}$C, $^{15}$N, $^{31}$P, $^{32}$P, $^{33}$P, $^{35}$S, $^{65}$Ga, $^{99}$mTc (Tc-99m), $^{111}$In, $^{123}$I, $^{125}$I, $^{169}$Yb and $^{186}$Re.

In some embodiments of the invention, the tag is a fluorescent label such as a fluorophore. A variety of known fluorophores can be employed in the practice of the invention. (See, for example, The Handbook: Fluorescent Probes and Labeling Technologies, 10th edition (2005), Invitrogen, Carlsbad, Calif., the entire contents of which are incorporated herein by reference). Fluorophores that may be used in fluorescent tags include fluorescein, rhodamine, phycobiliproteins, cyanine, coumarin, pyrene, green fluorescent protein, BODIPY®, and their derivatives. Both naturally occurring and synthetic derivatives of fluorophores can be used. Examples of fluorescein derivatives include fluorescein isothiocyanate (FITC), Oregon Green, Tokyo Green, seminapthofluorescein (SNAFL), and carboxynaphthofluorescein. Examples of rhodamine derivatives include rhodamine B, rhodamine 6G, rhodamine 123, tetramethyl rhodamine derivatives TRITC and TAMRA, sulforhodamine 101 (and its sulfonyl chloride form Texas Red), and Rhodamine Red. Phycobiliproteins include phycoerythrin, phycocyanin, allophycocyanin, phycoerythrocyanin, and peridinin chlorophyll protein (PerCP). Types of phycoerythrins include R-phycoerythrin, B-phycoerythrin, and Y-phycoerythrin. Examples of cyanine dyes and their derivatives include Cy2 (cyanine), Cy3 (indocarbocyanine), Cy3.5, Cy5 (indodicarbocyanine), Cy5.5, Cy7, BCy7, and DBCy7. Examples of green fluorescent protein derivatives include enhanced green fluorescent protein (EGFP), blue fluorescent protein (BFP), cyan fluorescent protein (CFP), and yellow fluorescent protein (YFP). BODIPY® dyes (Invitrogen) are named either for the common fluorophore for which they can substitute or for their absorption/emission wavelengths. BODIPY® dyes include BODIPY FL, BODIPY R6G, BODIPY TMR, BODIPY TR, BODIPY 581/591, BODIPY 630/650, and BODIPY 650/665.

Alexa Fluor® dyes (Invitrogen) are also suitable for use in accordance with inventive methods and compounds. Alexa Fluor® dyes are named for the emission wavelengths and include Alexa Fluor 350, Alex Fluor 405, Alexa Fluor 430, Alexa Fluor 488, Alex Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750 and AlexaFlour 790. In some embodiments, the fluorescent tag is a dylight or irdyes used with the Licor Odyssey.

Kits

In another aspect, the present invention provides a kit for assaying the inhibitory activity of a compound on the self-cleavage of HCV NS3. Such kits include at least one HCV NS3, or a variant thereof. In certain embodiments, a provided kit can further include a tagged version of at least one HCV NS3, or a variant thereof. In certain embodiments, such kits include all the reagents necessary to assay a test compound or library of test compounds. A provided kit may include cell lines, media, growth factors, DNA constructs, etc.

In certain embodiments, a provided kit includes instructions for contacting a test compound with at least one HCV NS3, or a variant thereof. For example, the kit may include instructions for contacting a test compound with a replicon cell or re-engineered replicon cell. In some embodiments, the instructions may require mixing a test compound with recombinant or isolated NS3 and NS4A. In another embodiment, the instructions may require mixing about 100 nM/well of the test compound with about 50 µg/well of at least one HCV NS3, or a variant thereof.

The instructions may also suggest leaving the reaction between the components of the kit to progress for a certain period of time, e.g., 1, 2, 3, 4, 5 or more hours. In one embodiment, the instructions may suggest a reaction time of between 1 and 3 hours. In one embodiment, the instructions may suggest a reaction time of about 16 hours.

DEFINITIONS

As used herein, the term "inhibitor" is defined as a compound that binds to and/or inhibits HCV protease with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

The terms "measurable affinity" and "measurably inhibit," as used herein, mean a measurable change in HCV protease activity between a sample comprising a compound identified by methods of the present invention, or composition thereof, and HCV protease, and an equivalent sample comprising HCV protease, in the absence of said compound, or composition thereof.

As used herein, the term "irreversible" or "irreversible inhibitor" refers to an inhibitor (i.e. a compound) that is able to be covalently bonded to HCV protease in a substantially non-reversible manner. That is, whereas a reversible inhibitor is able to bind to (but is generally unable to form a covalent bond with) HCV protease, and therefore can become dissociated from the HCV protease, an irreversible inhibitor will remain substantially bound to HCV protease once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to HCV protease once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with HCV protease, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

As used herein, the term "construct" refers to any polynucleotide that has been manipulated by the hand of man. Specifically, the construct is isolated from other sequences that are found in the natural state. The construct may be produced by recombinant techniques known in the art such as the polymerase chain reaction. In certain embodiments, the polynucleotide contains various elements that are operably linked, and the construct is introduced into a cell. For example, the construct may contain a promoter operably linked to a coding sequence, and the construct may be introduced into a cell to cause the cell to produce the encoded protein. In some embodiments, the construct has been created or engineered by the hand of man and does not occur naturally.

As used herein, the term "polynucleotide" or "oligonucleotide" refers to a polymer of nucleotides. In some embodiments, a polynucleotide comprises at least three nucleotides, at least 10 nucleotides, or at least 100 nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, C5-bromouridine, C5-fluorouridine, C5-iodouridine, C5-propynyl-uridine, C5-propynyl-cytidine, C5-methylcytidine, 7-deazadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

According to the present invention, a "protein" comprises a polymer of amino acid residues linked together by peptide bonds. The term, as used herein, refers to proteins, polypeptides, and peptides of any size, structure, or function. Typically, a protein will be at least three amino acids long. Peptide may refer to an individual peptide or a collection of peptides. Provided peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a provided peptide may be modified, for example, by the addition of a chemical entity such as a carbohydrate group, a phosphate group, a hydroxyl group, a farnesyl group, an isofarnesyl group, a fatty acid group, a linker for conjugation, functionalization, or other modification, etc. A protein may also be a single molecule or may be a multi-molecular complex. A protein may be a fragment of a naturally occurring protein or peptide. A protein may be naturally occurring, recombinant, or synthetic, or any combination of these.

As used herein, the term "reporter gene" refers to a gene whose transcript or any other gene product (e.g., protein) is detectable. In some embodiments, the gene product is also quantifiable. In certain embodiments, the gene product is detectable using a standard assay. In certain embodiments, the reporter gene encodes a fluorescent or luminescent protein or an enzyme whose activity is detectable and quantifiable.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Test Compounds

Compounds to be screened in a method according to the present invention may be provided by any means known in the art. Test compounds include polynucleotides, peptides, proteins, small molecules, organic molecules, inorganic molecules, peptidomimetics, antibodies, or other chemical compounds. Such compounds may be prepared by purification or isolation from a source (e.g., plant, fungus, animal, bacteria, soil sample, etc.), or by synthesis. Synthesized compounds may be created by more conventional one-by-one synthetic methods or by combinatorial chemistry methods through rapid parallel and/or automated synthesis. Test compounds may be provided in crude or pure forms. Test compounds may be natural products or derivatives of natural products. In certain embodiments, test compounds are provided as libraries of chemical compounds. One of ordinary skill in the art will appreciate that such libraries are readily available commercially. Alternatively, a library of test compounds can be a proprietary "in-house" library of compounds.

Test compounds are screened by the methods described above to identify inhibitors of HCV NS3. Chemical inhibitors of HCV NS3 are useful in diseases and disorders associated with HCV as described herein. In some embodiments, a known inhibitor of HCV NS3 can be used as a comparator compound.

Compound 1, also known as VX-950, is an HCV NS3 inhibitor currently under development in human clinical trials.

Exemplary compounds identified as inhibitors of HCV NS3 by methods of the present invention are set forth below:

Compound 1

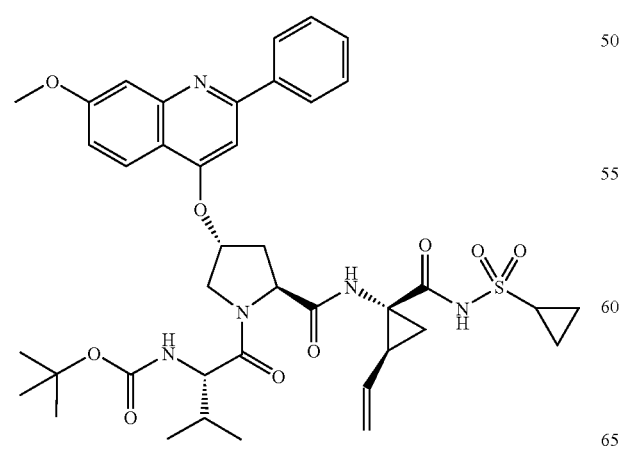

Compound 2

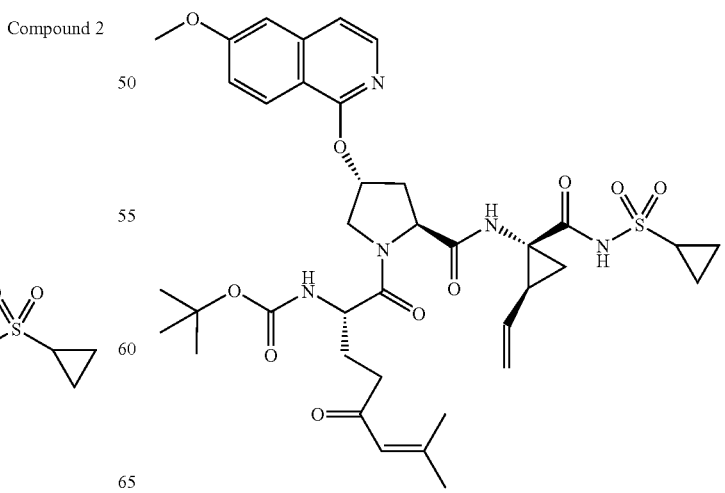

Compound 3

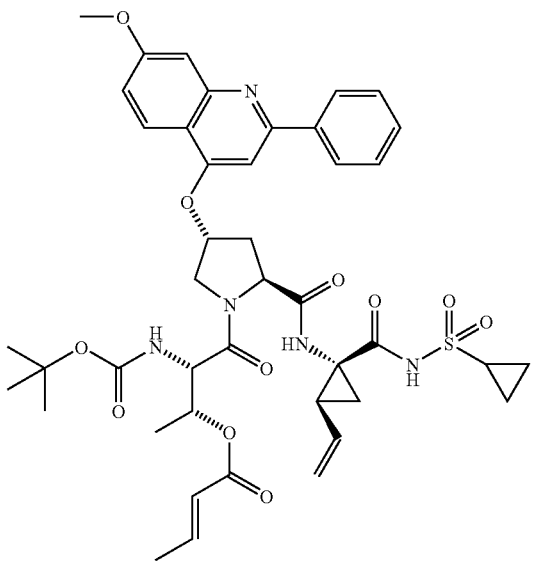

Compound 4

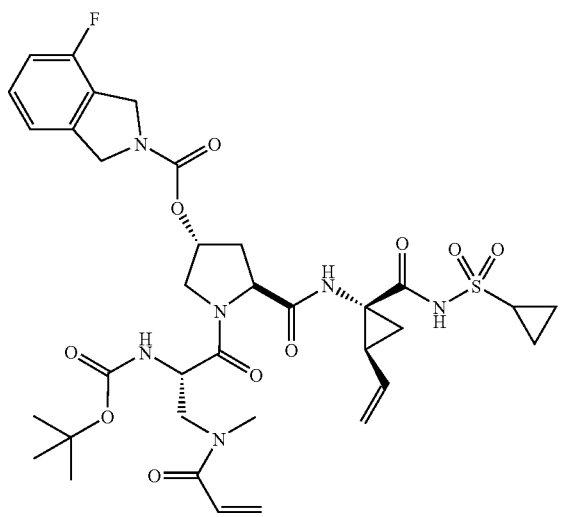

Compound 5

Compound 6

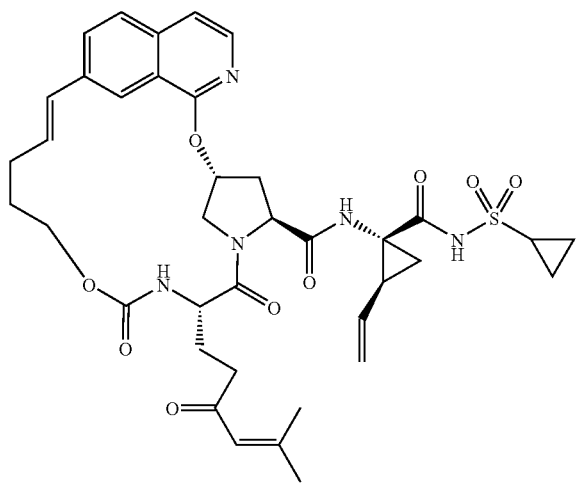

Compound 7

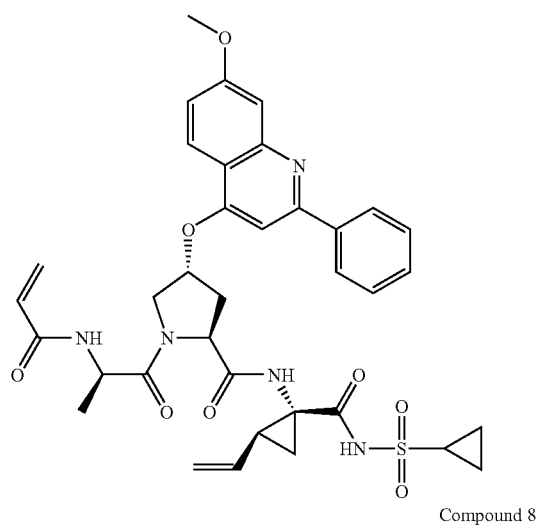

Compound 8

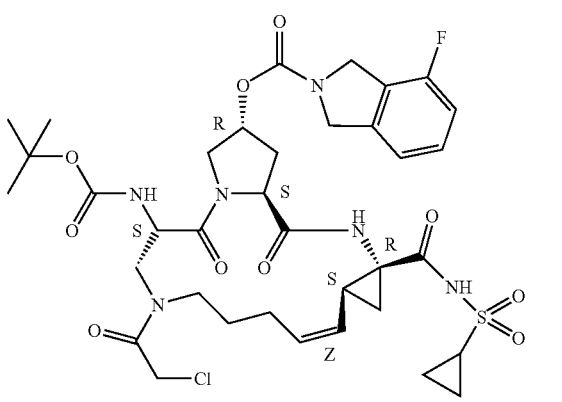

Uses, Formulation and Administration

Pharmaceutically Acceptable Compositions

According to another embodiment, the invention provides a composition comprising a compound identified using methods of this invention, or a pharmaceutically acceptable salt thereof, and a pharmaceutically acceptable carrier, adjuvant, or vehicle. The amount of compound in compositions of this invention is such that is effective to measurably inhibit HCV protease, or a mutant thereof, in a biological sample or in a patient. In certain embodiments, the amount of compound in compositions of this invention is such that is effective to measurably inhibit HCV protease, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising compounds identified by methods of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds identified by methods of the present invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds identified by methods of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

In some embodiments, a provided composition is administered to a patient in need thereof once daily. Without wishing to be bound by any particular theory, it is believed that prolonged duration of action of an irreversible inhibitor identified by provided methods, is particularly advantageous for once daily administration to a patient in need thereof for the treatment of a disorder associated with HCV NS3 protease. In certain embodiments, a provided composition is administered to a patient in need thereof at least once daily. In other embodiments, a provided composition is administered to a patient in need thereof twice daily, three times daily, or four times daily.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound identified by methods of the present invention in the composition will also depend upon the particular compound in the composition.

Uses of Compounds and Pharmaceutically Acceptable Compositions

Compounds and compositions described herein are generally useful for the inhibition of HCV protease activity and/or the activity of a mutant thereof. Thus, provided compounds, identified by methods of the present invention, are useful for treating non-A, non-B hepatitis, including hepatitis C.

According to another embodiment, the invention relates to a method of inhibiting HCV protease, or a mutant thereof, activity in a patient comprising the step of administering to said patient a compound identified by methods of the present invention, or a composition comprising said compound. According to certain embodiments, the invention relates to a method of irreversibly inhibiting HCV protease, or a mutant thereof, activity in a patient comprising the step of administering to said patient a compound identified by methods of the present invention, or a composition comprising said compound. In other embodiments, the present invention provides a method for treating a disorder mediated by HCV protease, or a mutant thereof, in a patient in need thereof, comprising the step of administering to said patient a compound identified by methods according to the present invention or pharmaceutically acceptable composition thereof. Such disorders are described in detail herein.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a compound identified by methods of the present invention, or composition thereof, is administered in combination with another inhibitor of HCV protease, or a variant thereof. In some embodiments, a compound identified by methods of the present invention, or composition thereof, is administered in combination with another antiviral agent. Such antiviral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors, e.g. BILN 2061 and VX-950); inhibitors of other targets in the HCV life cycle, including helicase and polymerase inhibitors; inhibitors of internal ribosome entry; broad-spectrum viral inhibitors, such as IMPDH inhibitors (e.g., mycophenolic acid and derivatives thereof); or combinations of any of the above.

In certain embodiments, a combination of 2 or more antiviral agents may be administered. In certain embodiments, a combination of 3 or more antiviral agents may be administered. In some embodiments, the antiviral agents are selected from ribavirin or interferon. In other embodiments, the antiviral agent is α-interferon.

Other examples of agents the inhibitors of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, compounds identified by methods of the present invention, or a pharmaceutically acceptable composition thereof, are administered in combination with a monoclonal antibody or an siRNA therapeutic.

Those additional agents may be administered separately from a composition containing a compound identified by methods of the present invention, as part of a multiple dosage regimen. Alternatively, those agents may be part of a single dosage form, mixed together with a compound identified by methods of the present invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound identified by methods of the present invention may be administered with another therapeutic agent simultaneously or sequentially in separate unit dosage forms or together in a single unit dosage form.

Accordingly, the present invention provides a single unit dosage form comprising a compound identified by methods of the present invention, an additional therapeutic agent, and a pharmaceutically acceptable carrier, adjuvant, or vehicle.

The amount of both, a compound identified by methods of the present invention and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and a compound identified by methods of the present invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Methods for preparing exemplary inhibitor compounds, including Compound 2, Compound 3, Compound 4, Compound 5, Compound 6, Compound 7, and Compound 8, are described in detail in the following U.S. patent application U.S. Ser. No. 12/339,680, filed Dec. 19, 2008, and United States patent application publication 2009/0176858, the entirety of each of which is hereby incorporated herein by reference.

Materials and Methods

EXAMPLE 1

Single Chain HCV Protease (Wt) Peptide Expression and Purification

Wild type HCV protease was obtained from Bioenza (Mountain View, Calif.) and may also be prepared as described below.

The single-chain proteolytic domain (NS4A$_{21-32}$-GSGS-NS$_{33-631}$) was cloned into pET-14b (Novagen, Madison, Wis.) and transformed into DH10B cells (Invitrogen). The resulting plasmid was transferred into *Escherichia coli* BL21 (Novagen) for protein expression and purification. Briefly, the cultures were grown at 37° C. in LB medium containing 100 μg/mL of ampicillin until the optical density at 600 nm (OD600) reached 1.0 and were induced by addition of isopropyl-β-D-thiogalactopyranoside (IPTG) to 1 mM. After an additional incubation at 18° C. for 20 h, bacteria were harvested by centrifugation at 6,000×g for 10 min and resuspended in a lysis buffer containing 50 mM Na$_3$PO$_4$, pH 8.0, 300 mM NaCl, 5 mM 2-mercaptoethanol, 10% glycerol, 0.5% Igepal CA630, and a protease inhibitor cocktail consisting of 1 mM phenylmethylsulfonyl fluoride, 0.5 µg/mL leupeptin, pepstatin A, and 2 mM benzamidine. Cells were lysed by freezing and thawing, followed by sonication. Cell debris was removed by centrifugation at 12,000×g for 30 min. The supernatant was further clarified by passing through a 0.45-µm filter (Corning) and then loaded onto a HiTrap chelating column charged with NiSO$_4$ (Amersham Pharmacia Biotech). The bound protein was eluted with an imidazole solution in a 100-to-500 mM linear gradient. Selected fractions were run through Ni$^{2+}$ column chromatography and were analyzed on a 10% sodium dodecyl sulfate (SDS)-polyacrylamide gel. The purified protein was resolved by electrophoresis in a 12% SDS-PAGE gel and then transferred onto a nitrocellulose membrane. The protein was analyzed by Western blot analysis using monoclonal antibodies against NS3. Proteins were visualized by using a chemiluminescence kit (Roche) with horseradish peroxidase-conjugated goat anti-mouse antibodies (Pierce) as secondary antibodies. The protein was aliquoted and stored at –80° C.

EXAMPLE 2

Cloning and Expression of HCV Protease A156S, A156T, D168A, D168V Drug-Resistance Mutants and C159S Variant The mutant DNA fragments of NS4A/NS3 were generated by PCR and cloned into pET expression vector. After transformation into BL21 competent cells, the expression was induced with IPTG for 2 hours. The His-tagged fusion proteins were purified using affinity column followed by size exclusion chromatography.

EXAMPLE 3

In Vitro Transcription

In vitro transcripts of HCV positive strands were generated by using the protocol described by Lohmann V et al 2003. For transcription of positive-strand HCV RNAs, plasmid DNA (pFK 1341 PI-Luc/NS3-3'/ET, obtained from ReBLikon Gmbh (Heidelberg, Germany), was digested with AseI followed by Sca1. After restriction digest, DNA was extracted with phenol and chloroform, precipitated with ethanol, and dissolved in RNase-free water. In vitro transcription reactions contained 80 mM HEPES (pH 7.5), 12 mM MgCl$_2$, 2 mM spermidine, 40 mM dithiothreitol, a 3.125 mM concentration of each nucleoside triphosphate, 1 U of RNasin. 5 µg of restricted plasmid DNA and 80 U of T7 RNA polymerase (Promega) was used. After 2 h at 37° C., an additional 40 U of T7 polymerase was added, and the reaction was incubated for another 2 h. Transcription was terminated by the addition of 1 U of RNase-free DNase (Promega) per µg of plasmid DNA, followed by incubation for 30 min at 37° C. After extraction with acidic phenol and chloroform, RNA was precipitated with isopropanol and dissolved in RNase-free water. The concentration was determined by measurement of the optical density at 260 nm (OD260), and RNA integrity was checked by denaturing agarose gel electrophoresis.

EXAMPLE 4

Transfection of HCV Full Length Genome and Selection of Stable Cell Lines

7×10$^4$ Huh7-Lunet cells were seeded over night in a 12 well plate, the next day 1 µg of RNA/well was transfected using Mirus Tx (Madison, Wis.) kit. Transfection was performed according to manufacturer's instructions, and 24 hours after transfection cells were either subjected to Luciferase assay or subjected to G418 (400 µg/mL) selection in order to establish stable cell lines.

Cell Culture

Huh-luc/neo-ET, Huh7-Lunet were obtained from ReBLikon Gmbh (Heidelberg, Germany). Cells were grown in Dulbecco modified Eagle medium (DMEM; Invitrogen) supplemented with 2 mM L-glutamine, nonessential amino acids, 100 U of penicillin/mL, 100 µg of streptomycin/mL, and 10% fetal bovine serum. G418 (Geneticin; Invitrogen) was added at a final concentration of 400 µg/mL. Huh7-Lunet were grown in the absence of G418.

Mutant Constructs

Constructs containing clinically relevant mutations were generated by performing site-directed mutagenesis on the pFK-1389-luc-ubi-neo-NS3-3'ET plasmid (ReBLikon Gmbh (Heidelberg, Germany)). using the QuickChange II Site-Directed Mutagenesis Kit (Stratagene, La Jolla, Calif.) according to manufacturer's directions and with the primers described in Table 2.

TABLE 2

Primer sequence used to establish Mutant Replicon cell lines.

| | | |
|---|---|---|
| NS3-A156S-F | GCTGTGGGCATCTTTCGGTCTGCCGT GTGCACCCGAGGG | SEQ ID NO: 63 |
| NS3-A156S-R | CCCTCGGGTGCACACGGCAGACCGAA AGATGCCCACAGC | SEQ ID NO: 64 |
| NS3-A156T-F | GCTGTGGGCATCTTTCGGACTGCCGT GTGCACCCGAGGG | SEQ ID NO: 65 |
| NS3-A156T-R | CCCTCGGGTGCACACGGCAGTCCGAA AGATGCCCACAGC | SEQ ID NO: 66 |
| NS3-D168A-F | GGGGTTGCGAAGGCGGTGGCCTTTGT ACCCGTCGAGTCT | SEQ ID NO: 67 |
| NS3-D168A-R | AGACTCGACGGGTACAAAGGCCACCG CCTTCGCAACCCC | SEQ ID NO: 68 |
| NS3-D168V-F | GGGGTTGCGAAGGCGGTGGTCTTTGT ACCCGTCGAGTCT | SEQ ID NO: 69 |
| NS3-D168V-R | AGACTCGACGGGTACAAAGACCACCG CCTTCGCAACCCC | SEQ ID NO: 70 |
| NS3-C159S-F | ATCTTTCGGGCTGCCGTGAGCACCCG AGGGGTTGCGAAG | SEQ ID NO: 71 |
| NS3-C159S-R | CTTCGCAACCCCTCGGGTGCTCACGG CAGCCCGAAAGAT | SEQ ID NO: 72 |
| NS3-R155K-F | CACGCTGTGGGCATCTTTAAGGCTGC CGTGTGCACCCGA | SEQ ID NO: 73 |
| NS3-R155K-R | TCGGGTGCACACGGCAGCCTTAAAGA TGCCCACAGCGTG | SEQ ID NO: 74 |

Assay Protocols

EXAMPLE 5

HCV Protease Inhibition Assay Protocols Utilizing Secondary Reporter

Method A: qRT-PCR

The compounds were assayed to evaluate the antiviral activity and cytotoxicity of compounds in vitro using HCV RNA replicons. This assay used the cell line ET (luc-ubi-neo/ET), which is a human Huh7 hepatoma cell line that contains an HCV RNA replicon with a stable luciferase (Luc) reporter and cell culture-adaptive mutations. The HCV RNA levels were directly measured by viral specific TaqMan RT-PCR:

```
Forward primer:
                                    (SEQ ID NO: 75)
ACGCAGAAAGCGTCTAGCCAT Reverse primer:
                                    (SEQ ID NO: 76)
TACTCACCGGTTCCGCAGA Probe:
                                    (SEQ ID NO: 77)
[6-FAM]-CCTGGAGGCTGCACGACACTCAT-[TAMRA]
```

The ET cell line was grown in Dulbecco's modified essential media (DMEM), 10% fetal bovine serum (FBS), 1% penicillin-streptomycin (pen-strep), 1% glutamine, 250 µg/mL G418 in a 5% $CO_2$ incubator at 37° C. All cell culture reagents were obtained from Mediatech (Manassas, Va.). Cells were trypsinized (1% trypsin:EDTA) and plated out at $5\times10^3$ cells/well in white 96-well assay plates (Costar) dedicated to cell number (cytotoxicity) or antiviral activity assessments. Drugs were added at six 3-fold concentrations each and the assay was run in DMEM, 5% FBS, 1% pen-strep, 1% glutamine. Human interferon alpha-2b (PBL Biolabs, New Brunswick, N.J.) was included in each run as a positive control compound. Cells were processed 72 hr post drug addition when the cells are still subconfluent. Antiviral activity was measured by analyzing replicon-derived luciferase activity using the Steady-Glo Luciferase Assay System (Promega, Madison, Wis.) according to manufacturer's instruction. The number of cells in each well was determined by CytoTox-1 reagent (Promega). Compound profile was derived by calculating applicable $EC_{50}$ (effective concentration inhibiting virus replication by 50%), $EC_{90}$ (effective concentration inhibiting virus replication by 90%), $IC_{50}$ (concentration decreasing cell viability by 50%) and $SI_{50}$ (selective index: $EC_{50}/IC_{50}$) values. $IC_{50}$ values for selected compounds are set forth in Table 3, below.

Method B: HCV Protease FRET Assay for Wild Type and Mutated NS3/4A 1b Enzymes ($IC_{50}$)

A quantitative, fluorescence resonance energy transfer (FRET)-based methodology was employed to identify HCV NS3/4A protease inhibitors. The assay employed a synthetic FRET peptide, derived from the HCV NS5A/5B cleavage site, with the HCV protease to evaluate the activity of compounds against the protease by monitoring the cleavage activity of the complex. A synthetic peptide which encompasses the NS5A-5B junction (NH2-EDVVCCSMSYK-COOH) (SEQ ID NO: 78) was labeled with Dabcyl and Edans at N- and C-termini, respectively (Invitrogen, Carlsbad, Calif.). Fluorescence measurement was used to estimate the $IC_{50}$ value of the test compound. The two fluorophores form a quenching pair and exhibit FRET within the intact peptide. Upon cleavage of the FRET peptide by HCV NS3/4A proteinase complex (100 ng/mL), the fluorescence is recovered and can be continuously monitored at excitation/emission=340/490 nm.

Assay buffer: 2% CHAPS, 50 mM Tris pH 7.5, 50% glycerol, 2 uM M-2235 (Bachem) substrate. In a 50 µl reaction, add 49 µl assay buffer, 1 µl (1 U) HCV serine protease (Bioenza). Incubate 20 minutes at room temperature. The plate was read at either 350/460 nm (excitation/emission) on a fluorescent micro-plate reader or monitored at one-minute intervals to achieve the kinetic curve.

Method C: Luciferase Reporter Assay Protocol

The compounds were assayed to evaluate the antiviral activity and cytotoxicity of compounds using replicon-derived luciferase activity. This assay used the cell line ET (luc-ubi-neo/ET), which is a human Huh7 hepatoma cell line that contains an HCV RNA replicon with a stable luciferase (Luc) reporter and three cell culture-adaptive mutations. The ET cell line was grown in a 5% $CO_2$ incubator at 37° C. in Dulbecco's modified essential media (DMEM), supplemented with 2 mM L-glutamine ("1%"), nonessential amino acids, 100 U of penicillin/mL, 100 µg of streptomycin/mL ("1%"), 10% fetal bovine serum and 400 µg/mL G418 (Geneticin; Invitrogen).

All cell culture reagents were obtained from Invitrogen (Carlsbad). Cells were trypsinized (1% trypsin:EDTA) and plated out at $5\times10^3$ cells/well in white 96-well assay plates (Costar) dedicated to cell number (cytotoxicity) or antiviral activity assessments. Test compounds were added at six 3-fold serial dilutions each and the assay was run in DMEM, 5% FBS, 1% pen-strep, 1% glutamine, 1% non essential amino acid. Human interferon alpha-2b (PBL Biolabs, New Brunswick, N.J.) was included in each run as a positive control compound. Cells were processed 72 hr post test compound addition when the cells were still subconfluent. Antiviral activity was measured by analyzing replicon-derived luciferase activity using the Steady-Glo Luciferase Assay System (Promega, Madison, Wis.) according to manufacturer's instruction. The number of cells in each well was determined by Cell Titer Blue Assay (Promega). Compound profile was derived by calculating applicable $EC_{50}$ (effective concentration inhibiting virus replication by 50%), $EC_{90}$ (effective concentration inhibiting virus replication by 90%), $IC_{50}$ (concentration decreasing cell viability by 50%) and $SI_{50}$ (selective index: $EC_{50}/IC_{50}$) values.

EXAMPLE 6

HCV Protease FRET Assay for Mutated NS3/4A 1b Enzymes

The protocol is a modified FRET-based assay (v_02) from *In Vitro Resistance Studies of HCV Serine Protease Inhibitors*, 2004, JBC, vol. 279, No. 17, pp 17508-17514. Inherent potency of compounds was assessed against A156S, A156T, D168A, and D168V mutants of the HCV NS3/4A 1b protease enzyme as follows:

Assay buffer: 2% CHAPS, 50 mM Tris pH 7.5, 50% glycerol, 2 µM M-2235 (Bachem) substrate. In a 50 µl reaction, add 49 µl assay buffer, 1 µl (1 U) HCV serine protease (Bioenza). Incubate 20 minutes at room temperature. The plate was read at either 350/460 nm (excitation/emission) on a fluorescent micro-plate reader or monitored at one-minute intervals to achieve the kinetic curve.

10× stocks of NS3/4A protease enzyme from Bioenza (Mountain View, Calif.) and 1.13×5-FAM/QXL™520 FRET peptide substrate from Anaspec (San Jose, Calif.) were prepared in 50 mM HEPES, pH 7.8, 100 mM NaCl, 5 mM DTT and 20% glycerol. 5 µL of each enzyme were pre-incubated in a Corning (#3573) 384-well, black, non-treated microtiter plate (Corning, N.Y.) for 30 min at 25° C. with a 0.5 µL volume of 50% DMSO and serially diluted compounds prepared in 50% DMSO. Protease reactions were started with the addition of 45 µL of the FRET substrate and monitored for 120 minutes at $\lambda_{ex}487/\lambda_{em}514$ through Quad[4] monochromoters in a Synergy[4] plate reader from BioTek (Winooski, Vt.). At the conclusion of each assay, progress curves from each well were examined for linear reaction kinetics and fit statistics ($R^2$, absolute sum of squares). Initial velocity (0 minutes to 30+ minutes) from each reaction was determined from the slope of a plot of relative fluorescence units vs time (minutes) and then plotted against inhibitor concentration to estimate $IC_{50}$ from log[Inhibitor] vs Response, Variable Slope model in GraphPad Prism from GraphPad Software (San Diego, Calif.).

EXAMPLE 7

HCV Protease FRET Assay for WT and Mutated NS3/4A 1b Enzymes ($IC_{50\_APP}$)

The following protocol was used to generate "apparent" $IC_{50}$ ($IC_{50\_APP}$)) values as depicted in Table 3, below. Without wishing to be bound by any particular theory, it is believed that $IC_{50\_APP}$, contrasted with $IC_{50}$ values, may provide a more useful indication of time-dependent inhibition, and are thus more representative of binding affinity. The protocol is a modified FRET-based assay (v_03) developed to evaluate compound potency, rank-order and resistance profiles against wild type and C159S, A156S, A156T, D168A, D168V, R155K mutants of the HCV NS3/4A 1b protease enzyme as follows: 10× stocks of NS3/4A protease enzyme from Bioenza (Mountain View, Calif.) and 1.13×5-FAM/QXL™520 FRET peptide substrate from Anaspec (San Jose, Calif.) were prepared in 50 mM Tris-HCl, pH 7.5, 5 mM DTT, 2% CHAPS and 20% glycerol. 5 μL of each enzyme were added to Corning (#3575) 384-well, black, microtiter plates (Corning, N.Y.) after spotting a 0.5 μL volume of 50% DMSO and serially diluted compounds prepared in 50% DMSO. Protease reactions were immediately started after enzyme addition with the addition of 45 μL of the FRET substrate and monitored for 60-90 minutes at $\lambda_{ex}485/\lambda_{em}520$ in a Synergy$^4$ plate reader from BioTek (Winooski, Vt.). At the conclusion of each assay, progress curves from each well were examined for linear reaction kinetics and fit statistics ($R^2$, 95% confidence intervals, absolute sum of squares). Initial velocity (0 minutes to 15+ minutes) from each reaction was determined from the slope of a plot of relative fluorescence units vs time (minutes) and then plotted against inhibitor concentration as a percent of the no inhibitor and no enzyme controls to estimate apparent $IC_{50}$ from log[Inhibitor] vs Response, Variable Slope model in GraphPad Prism from GraphPad Software (San Diego, Calif.).

Table 3 shows the activity of selected compounds of this invention in the FRET Assay. The compound numbers correspond to the compound numbers in Table 3. Compounds having an activity designated as "A" provided an $IC_{50} \leq 10$ nM; compounds having an activity designated as "B" provided an $IC_{50} > 10$ nM and ≤100 nM; compounds having an activity designated as "C" provided an $IC_{50} > 100$ nM and ≤1000 nM; and compounds having an activity designated as "D" provided an $IC_{50} > 1000$ nM and <10,000 nM.

TABLE 3

Enzymatic Data for Exemplary Compounds

| Compound tested | Enzyme/Assay | Inhibition |
|---|---|---|
| Compound 3 | WT | A |
| | HCV A156S | A |
| | HCV A156T | C |
| | HCV D168A | C |
| | HCV D168V | D |
| | Replicon | A |
| | Replicon | A[1] |
| Compound 4 | WT | A |
| | HCV A156S | A |
| | HCV A156T | A |
| | HCV D168A | B |
| | HCV D168V | B |
| | HCV R155K | B |
| | Replicon[2] | A |
| | Replicon[2] | B[1] |
| Compound 5 | WT | A |
| | HCV A156S | A |
| | HCV D168A | C |
| | HCV R155K | B |
| | Replicon | A[3] |
| | Replicon | B[4] |
| Compound 6 | WT | A |
| | HCV A156S | B |
| | HCV D168A | D |
| | HCV R155K | B |
| | Replicon | A[3] |
| | Replicon | A[4] |
| Compound 7 | WT | A |
| | HCV A156S | A |
| | HCV A156T | B |
| | HCV D168A | B |
| | HCV D168V | C |
| | Replicon[2] | A |
| | Replicon[2] | A[1] |
| Compound 8 | WT | A |
| | HCV A156S | A |
| | HCV D168A | B |
| | HCV R155K | B |
| | Replicon | B[3] |
| | Replicon | C[4] |

[1]Designates $IC_{90}$ value (nM).
[2]Data collected from assay described in Example 5 (Method C).
[3]Designates $EC_{50}$ value (nM). Data collected from assay described in Example 5 (Method C).
[4]Designates $EC_{90}$ value (nM). Data collected from assay described in Example 5 (Method C).

EXAMPLE 8

Inhibition of Protease Self Cleavage

Huh-7-Luc-Neo-ET cells were plated in Replicon Assay Medium (RPMI supplemented with 5% FBS, 1× non-essential amino acids and pen/strep) at a density of 1×10$^5$ cells/well in 12 well plates. Eight hours later the media was removed and replaced with 1 mL media containing test compound (5 wells per compound) and 0.02% DMSO and the cells were returned to the incubator overnight. Sixteen hours later 1 well from each compound and 1 untreated well were washed with PBS, then lysed and scraped into 30 μL of Cell Extraction Buffer (Biosource, Camarillo, Calif.) plus Complete Protease Inhibitor (Roche, Indianapolis, Ind.). The remaining wells were rinsed 2× with PBS then fed with Replicon Media and returned to the incubator. Cells were washed once every hour by removing the old media and replacing it with fresh media and were lysed and collected at 4, 12, 24, and 48 hours following the first collection.

Cell lysates were separated by SDS-Page (4-20%) and transferred to Immobilon-P PVDF membrane (Millipore Corporation, MA) and blotted with polyclonal anti NS3 antibody (Bioenza, Calif.). Blots were scanned on an Odyssey infrared scanner from Licor and the FL band and cleavage products were quantified separately using the Licor software provided with the scanner. The cleavage product was calculated as a percentage of the total NS3 in each sample and then normalized to the DMSO control so that the DMSO control reflects 100% activity.

Results and Discussion

When protease activity is inhibited, self-cleavage is abolished and the only protein species detectable is the holoenzyme. After 16 hours of continuous exposure of the replicon cells to NS3 inhibitor compound, the self-cleavage products were undetectable in the treated samples, but readily detectable in the not treated control replicon cells. Prolonged duration of action was demonstrated by exposing the replicon cells to a protease inhibitor for 16 hours, at which time the compound was removed, and the replicon cells were repeatedly washed for several more hours. Covalent irreversible NS3 inhibitors demonstrated sustained inhibition of NS3 internal self-cleavage activity for up to 48 hours, whereas the protease self-cleavage activity rapidly returned when using reversible compounds (FIG. 4 and FIG. 5).

Specifically, FIG. 2 depicts luciferase activity, using a replicon assay, in the presence of varying concentrations of two HCV protease inhibitors, Compound 2 and Compound 3, at 24 h, 48 h and 96 h. Compound 2 is a non-covalent inhibitor whereas Compound 3 is an irreversible covalent inhibitor. Despite differences in the mechanism of action of the two compounds on the protease, the replicon assay shows similar results, due to the indirect nature of the assay readout.

Figure 3:
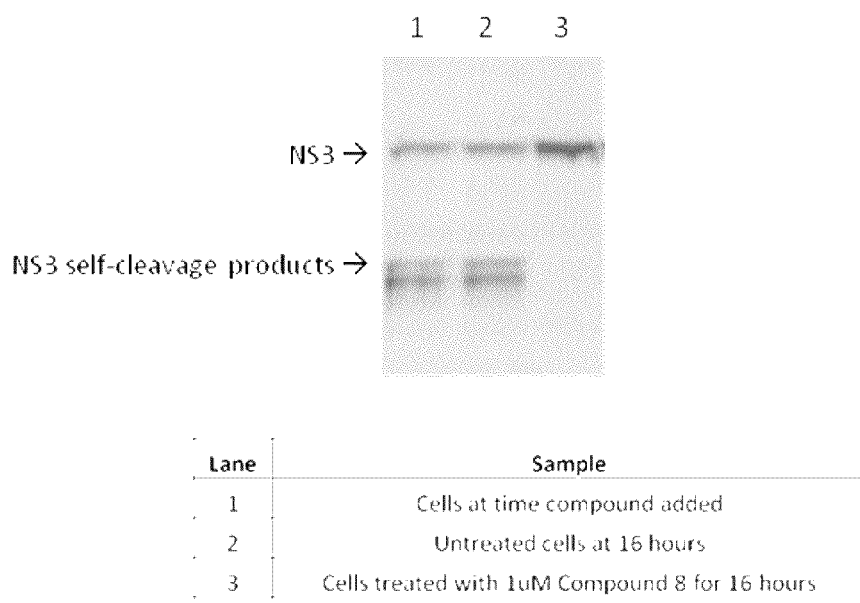
FIG. 3 depicts that the NS3 internal self-cleavage products are inhibited by treatment of replicon cells with Compound 8 for 16 hours.

FIG. 3 depicts that the NS3 internal self-cleavage products are inhibited by treatment of replicon cells with Compound 8 for 16 hours.

Figure 4:
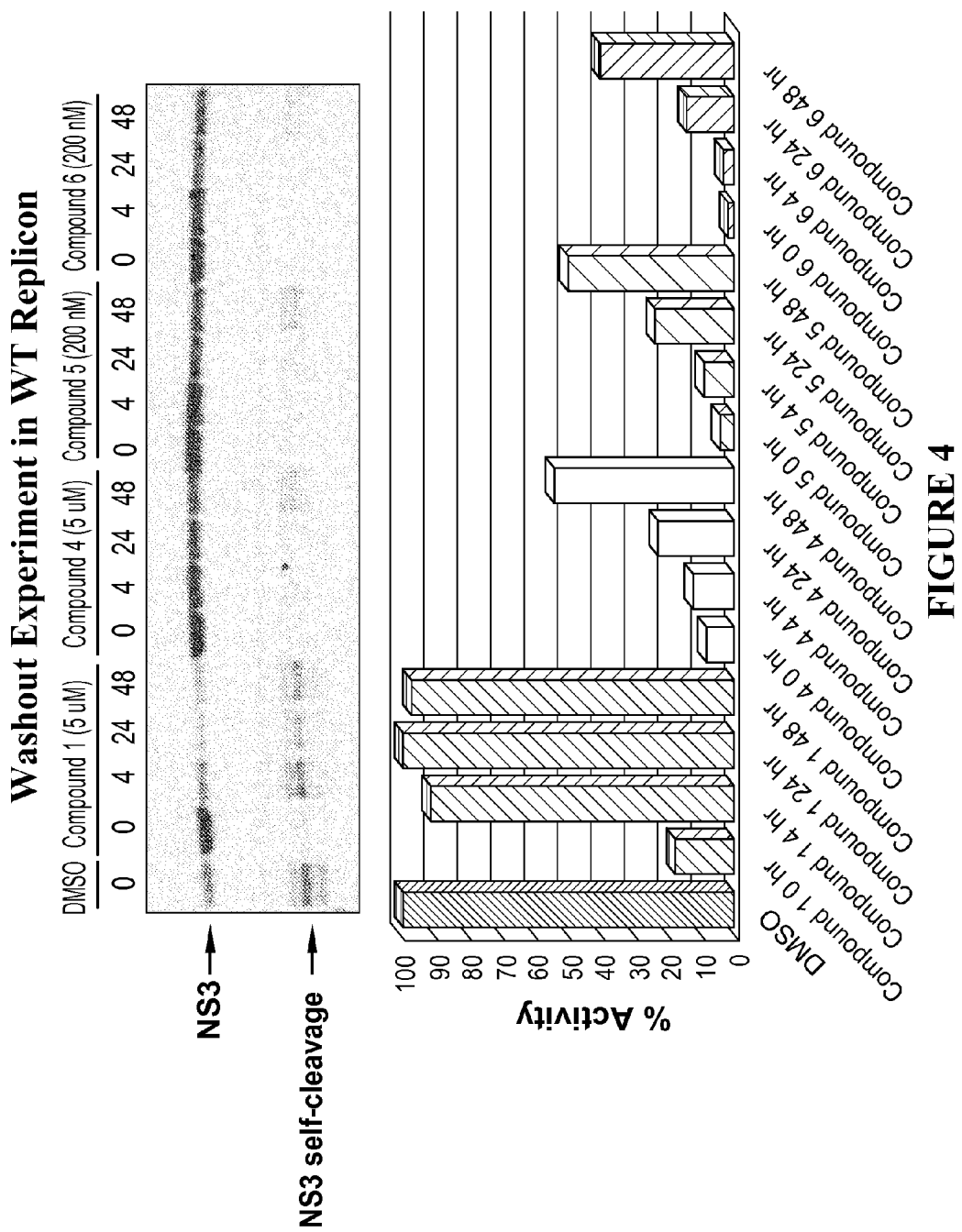
FIG. 4 depicts three irreversible covalent inhibitors of NS3 protease which demonstrate prolonged inhibition of NS3 protease activity in the wild type replicon cells, as measured by self-cleavage, after the compounds are removed. Compounds are incubated with replicon cells for 16 hours and then removed (time 0). Even up to 48 hours after removal of covalent NS3 inhibitors, NS3 self-cleaving activity is inhibited by at least 50%, whereas a reversible drug shows virtually complete return of activity in as little as 4 hours after drug removal.
Figure 5:
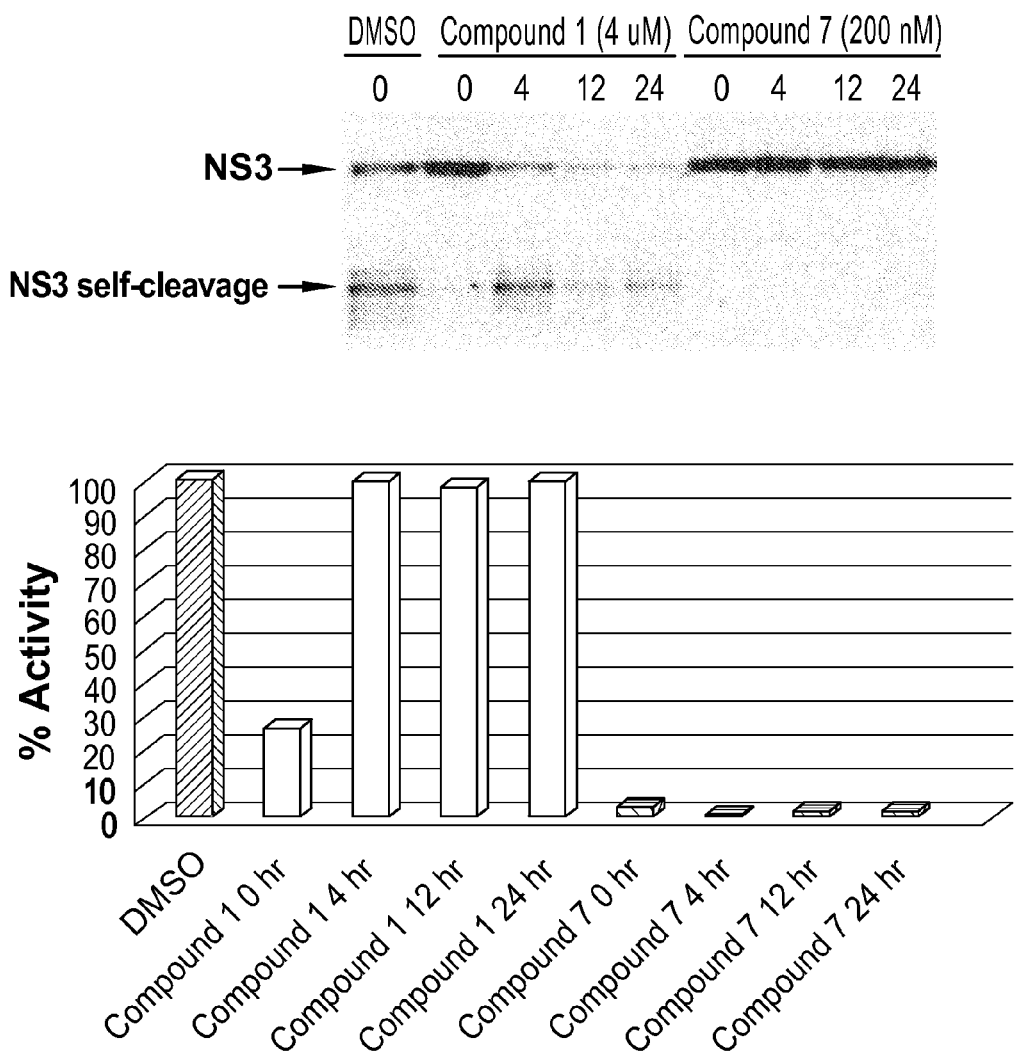
FIG. 5 depicts another covalent inhibitor of NS3 protease which demonstrates prolonged inhibition of NS3 protease activity in the wild type replicon cells, as measured by self-cleavage, up to 24 hours after the compound is removed. The irreversible covalent inhibitor demonstrates virtually complete inhibition up to 24 hours after compound removal whereas the reversible drug shows complete return of activity in as little as 4 hours after drug removal.

FIG. 4 depicts three irreversible covalent inhibitors (Compound 4, Compound 5, and Compound 6) of NS3 protease demonstrate prolonged inhibition of NS3 protease activity in the wild type replicon cells, as measured by self-cleavage, after the compounds are removed. Compounds were incubated with replicon cells for 16 hours and then removed (time 0). Even up to 48 hours after removal of covalent irreversible NS3 inhibitors, NS3 self-cleaving activity is inhibited by at least 50%, whereas a reversible drug, Compound 1, shows virtually complete return of activity in as little as 4 hours after drug removal.

FIG. 5 depicts another covalent inhibitor of NS3 protease, Compound 7, demonstrates prolonged inhibition of NS3 protease activity in the wild type replicon cells, as measured by self-cleavage, up to 24 hours after the compound is removed. The irreversible covalent inhibitor Compound 7 demonstrates virtually complete inhibition up to 24 hours after compound removal whereas the reversible drug, Compound 1, shows complete return of activity in as little as 4 hours after drug removal.

Figure 6:
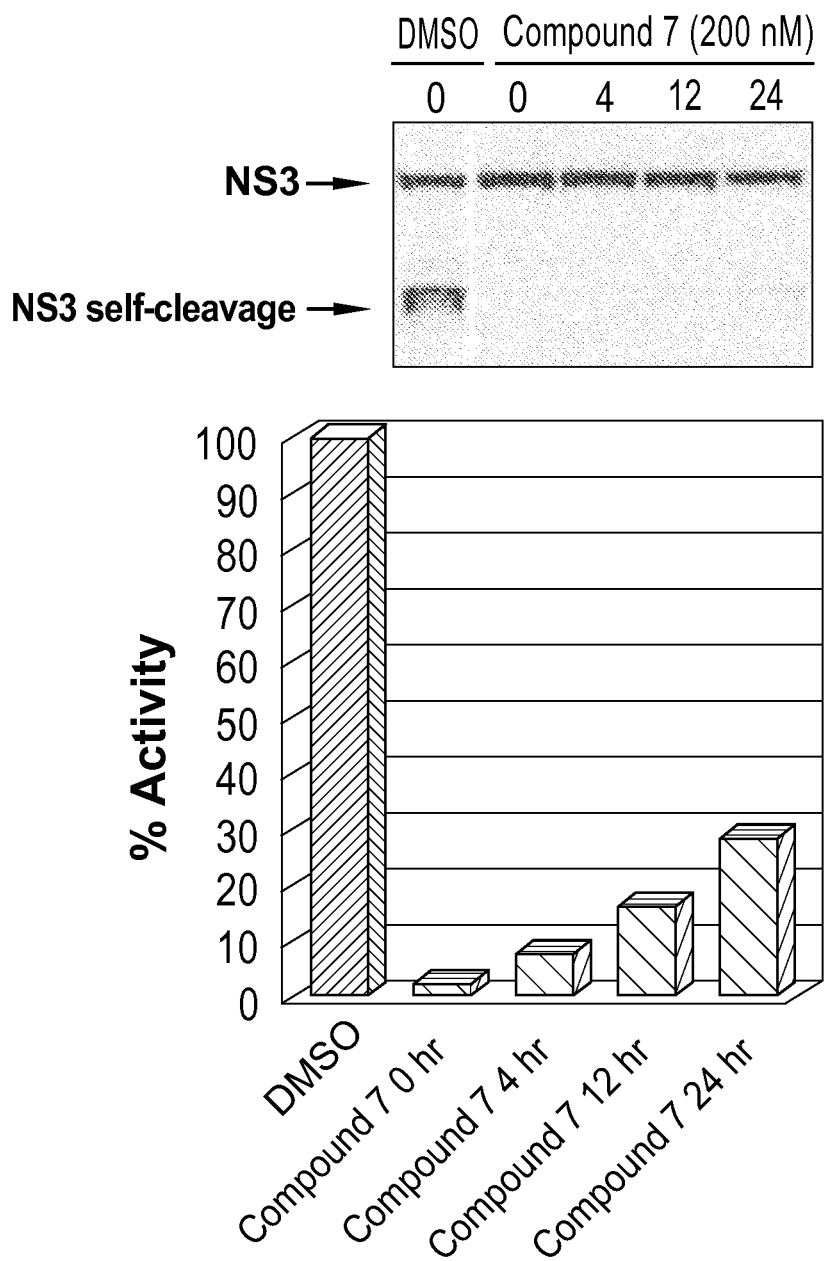
FIG. 6 depicts a covalent protease inhibitor which demonstrates prolonged inhibition of NS3 protease activity in modified replicon system where the NS3 protease contains a clinically observed mutation that alters an amino acid from arginine to lysine at position 155 (R155K). This mutation results in clinical drug resistance to protease inhibitors.

FIG. 6 depicts a covalent protease inhibitor, Compound 7, demonstrates prolonged inhibition of NS3 protease activity in modified replicon system where the NS3 protease contains a clinically observed mutation that alters an amino acid from arginine to lysine at position 155 (R155K). This mutation results in clinical drug resistance to protease inhibitors. FIG. 6 depicts that, even with this mutation, irreversible covalent drugs can inhibit activity from the mutant protease for at least 24 hours after compound removal.

EXAMPLE 9

Mass Spectrometric Analysis

Mass spectrometric analysis of HCV wild type or HCV variants (C159S, A156S, R155K, D168A, A156T, and D168V) in the presence of test compound was performed. 100 pmols of HCV wild type (Bioenza Calif.) was incubated with test compound for 1 hr and 3 hrs at 10-fold excess of test compound to protein. 1 µL aliquots of the samples (total volume of 4.24 µL) were diluted with 10 µL of 0.1% TFA prior to micro C4 ZipTipping directly onto the MALDI target using Sinapinic acid as the desorption matrix (10 mg/mL in 0.1% TFA:Acetonitrile 50:50). Analyses were performed on a Shimadzu Biotech Axima TOF (Shimadzu Instruments) matrix-assisted-laser desorption/ionization Time-of-Flight (MALDI-TOF) mass spectrometer. The same procedure was carried out on 100 pmols of HCV C159S mutant of HCV protease for 3 hrs at 10-fold excess of test compound to protein.

In addition, mass spectrometric analysis of HCV NS3/4A genotypes 1a, 1b, 2a, and 3a in the presence of test compound was performed using the above protocol.

After 3 hours reaction, measurable covalent modification by Compound 5 of each HCV NS3/4A genotype was observed.

For the HCV (D168V) mutant there is complete conversion via covalent modification by Compound 4 after 3 hours reaction time. The mass difference between the new species and the unreacted mutant is consistent with the mass of Compound 4.

For the HCV (A156S) mutant there is complete conversion via covalent modification by Compound 4 after 3 hours reaction time. The mass difference between the new species and the unreacted mutant is consistent with the mass of Compound 4.

For the HCV (R155K) mutant there is good conversion via covalent modification by Compound 4 after 3 hours reaction time. The mass difference between the new species and the unreacted mutant is consistent with the mass of Compound 4.

For the HCV (A156T) mutant there is complete conversion via covalent modification by Compound 4 after 3 hours reaction time. The mass difference between the new species and the unreacted mutant is consistent with the mass of Compound 4.

EXAMPLE 10

Protease Self Cleavage in NS3/4a Mutant

Mutant construct. NS3/4a was amplified by PCR from the replicon plasmid (pFK-I389-luc-ubi-neo-NS3-3'-ET) using Accuprime Pfx (Invitrogen) according to manufacturer's instructions and with primers that added a KpnI site to the 3' end and a stop codon followed by a KpnI site at the 5' end. (Forward Sequence=TAATAAGGTACCATGGCGCCTATT ACGGC CTAC (SEQ ID NO: 79), Reverse Sequence= TTATTAGGTACCCTAGCACTCTTCCATCTCATCGAA (SEQ ID NO: 80)). The PCR product was then digested with KpnI and inserted into the KpnI sites of pcDNA3.1 (+). The NS3/4a insert was excised from pcDNA3.1 using NheI and XbaI and inserted into the NheI and XbaI sites of pCI-Neo (Promega).

The S139A mutant was generated using the QuickchangeII XL Site-Directed Mutagenesis kit (Stratagene) according to manufacturers instructions and with primers that contained the S139A mutation. (Forward Sequence= TCCTACT-TGAAGGGCTCTGCGGGCGG TCCACTGCTCTGC (SEQ ID NO: 81) Reverse Sequence= GCAGAGCAGTG-GACCGCCCGCAGAGCCCTTC AAGTAGGA (SEQ ID NO: 82)).

Figure 7:
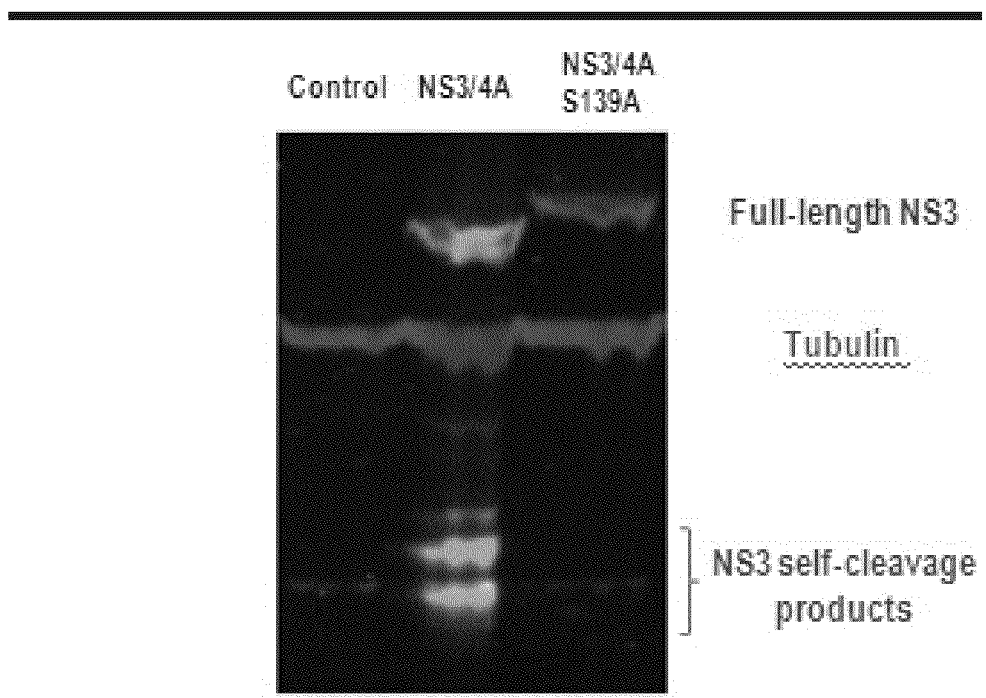
FIG. 7 depicts that NS3 protease activity is required for NS3 self-cleavage. Self-cleavage was observed in cells expressing WT NS3/4A (center lane) but not in mutant (S139A) NS3/4A cells (right lane).

NS3/4A S139A expression. HEK-293 cells were transfected with either WT-NS3/4A or NS3/4A-S139A. As depicted in FIG. 7, self-cleavage was observed in cells expressing WT NS3/4A but not in NS3/4A-S139A cells, demonstrating that NS3 protease activity is required for NS3 self-cleavage.

EXAMPLE 11

In Vivo Inhibition of Protease Self Cleavage

Male CD-1 mice (26-31 g) received an intravenous bolus of 20 μg cDNA in 2.5 mL of Minis TransIT solution administered via tail vein in 4-7 seconds (t=0 hr). One hour post cDNA injection (t=1 hr), mice were administered either vehicle (5% DMSO/10% Solutol HS 15/85% PBS) or test compound orally at 100 mg/kg. 8 hours post cDNA injection (t=8 hr), blood was collected via cardiac puncture and processed for plasma and liver samples were harvested, sectioned and snap frozen. Plasma and liver samples were collected from naïve mice as well for controls.

Anti-NS3 Western blots of liver protein lysate samples (100 μg per lane) showed inhibition of NS3 self-cleavage in mouse cohort treated with test compound. Untreated cohort NS3 self-cleavage inhibition ranged from −12 to 0% (negative number due to variation in samples and the inexactness of Western blot quantitation), while inhibition of NS3 self-cleavage in treated cohort ranged from 59 to 84%.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method comprising the steps of:
   (a) contacting a test compound with an NS3-containing protein;
   (b) measuring NS3 self-cleaving activity by measuring at least one of:
      (a) a level of NS3; and
      (b) a level of a NS3 self-cleavage product; and
   (c) classifying the test compound as a reversible or irreversible inhibitor of NS3;
   wherein:
      an irreversible inhibitor of NS3 is characterized by providing, when at a 5 uM concentration, at least 10% inhibition of NS3 self-cleaving activity four hours after removing the test compound; and
      a reversible inhibitor of NS3 is characterized by providing, when at a 5 uM concentration, less than 10% inhibition of NS3 self-cleaving activity four hours after removing the test compound.

2. A method comprising the steps of:
   (a) contacting a test compound with an HCV NS3-containing protein;
   (b) measuring HCV NS3 self-cleaving activity by measuring at least one of:
      (a) a level of HCV NS3; and
      (b) a level of a HCV NS3 self-cleavage product; and
   (c) classifying the test compound as a reversible or irreversible inhibitor of HCV NS3;
   wherein:
      an irreversible inhibitor of HCV NS3 is characterized by providing, when at a 5 uM concentration, at least 10% inhibition of HCV NS3 self-cleaving activity four hours after removing the test compound; and
      a reversible inhibitor of HCV NS3 is characterized by providing, when at a 5 uM concentration, less than 10% inhibition of HCV NS3 self-cleaving activity four hours after removing the test compound.

3. The method according claim 2, wherein said method is used to identify one or more reversible inhibitors of HCV NS3.

4. The method according to claim 2, wherein said method is used to identify one or more covalent irreversible inhibitors of HCV NS3.

5. The method according to claim 4, wherein said method is used to determine duration of action of the covalent irreversible inhibitor.

6. The method according to claim 2, wherein the HCV NS3 is selected from any one or more genotypes and subtypes.

7. The method according to claim 2, wherein the HCV NS3 is a variant.

8. The method according to claim 7, wherein the HCV NS3 is a variant selected from A156T, A156S, D168V, D168A, and R155K.

9. The method according to claim 4, wherein said irreversible inhibitor covalently modifies Cys159 of HCV protease subtype 1b, or a variant thereof 10. The method according to claim 2, further comprising the step of performing an additional method of determining inhibitory activity of the test compound.

11. The method according to claim 10, wherein the additional method is a method for confirming that the test compound is a covalent irreversible inhibitor.

12. The method according to claim 11, wherein the additional method is a washout experiment or mass spectrometric analysis.

13. A method comprising the steps of:
   (a) contacting a cell with a test compound;
   (b) washing said cells at one or more time intervals;
   (c) measuring HCV NS3 self-cleaving activity by measuring at least one of:
      (a) a level of HCV NS3; and
      (b) a level of a HCV NS3 self-cleavage product; and
   (d) classifying the test compound as a reversible or irreversible inhibitor of HCV NS3;
   wherein:
      an irreversible inhibitor of HCV NS3 is characterized by providing, when at a 5 uM concentration, at least 10% inhibition of HCV NSself-cleaving activity four hours after removing the test compound; and
      a reversible inhibitor of HCV NS3 is characterized by providing, when at a 5 uM concentration, less than 10% inhibition of HCV NS3 self-cleaving activity four hours after removing the test compound.

14. The method according to claim 13, wherein the cell is any cell line expressing both NS3 and NS4A.

15. The method according to claim 14, wherein the cell line is selected from Huh-7-Luc-Neo-ET cells, Huh-9-13 cells, Huh-5-15 cells, or Huh-11-7 cells.

16. The method according to claim 14, wherein the NS3 is a variant.

17. The method according to claim 15, wherein the Huh-7-Luc-Neo-ET cells comprise NS3 mutations A156T, A156S, D168V, D168A, and R155K.

18. The method according to claim 13, wherein the cells are washed at any time point between about 1 and 48 hours.

19. The method according to claim 2, wherein the method is repeated or performed with a plurality of different concentrations of the test compound.

20. The method according to claim 2, wherein the quantifying step involves direct measurement of HCV NS3 internal self-cleavage.

21. The method according to claim 13, wherein the quantifying step involves direct measurement of HCV NS3 internal self-cleavage.

22. The method according to claim 1, wherein the NS3-containing protein comprises NS3 and NS4A.

23. The method according to claim 2, wherein the HCV NS3-containing protein comprises NS3 and NS4A.

* * * * *